United States Patent [19]

Shibata et al.

[11] Patent Number: 5,348,976
[45] Date of Patent: Sep. 20, 1994

[54] CONDENSED HETEROCYCLIC DERIVATIVES AND AGRICULTURAL OR HORTICULTURAL FUNGICIDES CONTAINING THE SAME

[75] Inventors: Masaru Shibata; Shigekazu Ito; Jun-etsu Sakai; Shigeru Hayashi, all of Shizuoka, Japan

[73] Assignees: Kumai Chemical Industry Co., Ltd.; Ihara Chemical Industry Co., Ltd., both of Tokyo, Japan

[21] Appl. No.: 117,284

[22] Filed: Sep. 7, 1993

[30] Foreign Application Priority Data

Sep. 7, 1992 [JP] Japan .................. 4-262718
Jan. 28, 1993 [JP] Japan .................. 5-31117
Jul. 30, 1993 [JP] Japan .................. 5-208258

[51] Int. Cl.⁵ .......................................... A01N 43/10
[52] U.S. Cl. .................................. 514/469; 514/311; 514/419; 514/432; 514/443; 514/456; 546/168; 546/171; 546/175; 546/176; 548/491; 548/495; 548/500; 548/503; 548/504; 548/507; 549/23; 549/51; 549/57; 549/58; 549/404; 549/405; 549/407; 549/467
[58] Field of Search ............ 549/467, 58, 23, 51, 549/57, 404, 405, 407; 548/491, 503, 495, 500, 504, 507; 514/419, 443, 469, 456, 432, 311; 546/168, 171, 175, 176

[56] References Cited

U.S. PATENT DOCUMENTS

| | | | |
|---|---|---|---|
| 4,628,058 | 12/1986 | Rentzea et al. | 514/383 |
| 4,742,077 | 5/1988 | Stutz | 514/414 |
| 5,106,866 | 4/1992 | Maeda et al. | 514/443 |
| 5,134,140 | 7/1992 | Stack | 514/212 |

FOREIGN PATENT DOCUMENTS

| | | |
|---|---|---|
| 0398072 | 11/1990 | European Pat. Off. |
| 0425925 | 5/1991 | European Pat. Off. |
| 0477639 | 4/1992 | European Pat. Off. |
| 0493683 | 7/1992 | European Pat. Off. |

Primary Examiner—Glennon H. Hollrah
Assistant Examiner—B. Burn
Attorney, Agent, or Firm—Oblon, Spivak, McClelland, Maier & Neustadt

[57] ABSTRACT

The present invention provides a condensed heterocyclic derivative represented by a formula:

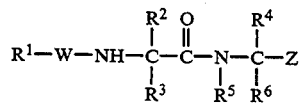

wherein $R^1$ represents a lower alkyl group, an alkenyl group, or the like, $R^2$, $R^3$, $R^4$, $R^5$, and $R^6$ independently represent a hydrogen atom, a lower alkyl, or the like, W is represented by $-OC(O)-$, $-SC(O)-$, or the like, and Z represents a 2-indolyl group or the like. The present invention also provides an agricultural or horticultural fungicide which comprises an amount of the condensed derivative known to be effective as a fungicide. The agricultural or horticultural fungicide according to the present invention exhibits a superior control effect for downy mildew and late blight, without harm to nonfungal, photosynthesizing plants.

6 Claims, No Drawings

CONDENSED HETEROCYCLIC DERIVATIVES AND AGRICULTURAL OR HORTICULTURAL FUNGICIDES CONTAINING THE SAME

FIELD OF THE INVENTION

The present invention relates to a condensed heterocyclic derivative as well as an agricultural or horticultural fungicide containing the same as an active ingredient. The present invention also relates to a process for preparing the condensed heterocyclic derivative.

BACKGROUND OF THE INVENTION

Heretofore, some aminoacid amide derivatives have been known as a pesticide and also as a herbicide. For instance, such aminoacid amide derivatives include N-(tert-butoxycarbonyl)-L-valine-4-methoxyphenylethylamide (Japanese Patent Application First Publication No. Hei 3-5,451), $N^2$-phenoxycarbonyl-$N^1$-[racemi-1-(4-chlorophenyl)ethyl]-L-isoleucinamide (Japanese Patent Application First Publication No. Hei 3-153,657), N-(isopropyl-oxycarbonyl)-L-valine-4-methoxyphenylethylamide (Japanese Patent Application First Publication No. Hei 4-230,652), $N^2$-phenoxycarbonyl-$N^1$-[racemi-1-(4-chlorophenyl)ethyl]-L-cyclopentylglycine (Japanese Patent Application First Publication No. Hei 4-230,653), $N^2$-sec-butyloxycarbonyl-$N^1$-[S(+)-1-cyclohexylethyl]-L-valinamide (Japanese Patent Application First Publication No. Hei 4-283,554), benzyl {(D,L)-1-[(3,4-dimethoxyphenethyl)-carbamoyl]-n-butyl}carbamate (Japanese Patent Application First Publication No. Hei 4-308,507), N-(i-propyloxycarbonyl)-L-valine-diphenylmethylamide (Japanese Patent Application First Publication No. Hei 4-338,372), and the like.

These conventional compounds, however, do not have sufficient effect to act as a pesticide. In addition, the prior an documents do not disclose an amino-acid amide derivative possessing a condensed heterocyclic ring such as a benzofuran ring, benzothiophene ring, or the like. Therefore, the utility of the aminoacid amide derivatives has not been known.

SUMMARY OF THE INVENTION

The objective of the present invention is to provide a novel condensed heterocyclic derivative exhibiting an excellent anti-fungal activity.

The present inventors have synthesized various condensed heterocyclic derivatives and have carried out extensive research in connection with their effects on the physiological activities of fungi. As a result, we have found that the compounds according to the present invention exhibit a broad spectrum of anti-fungal activity especially against downy mildew and late blight, and at the same time they do not harm the useful plant growth.

According to a first aspect of the present invention, there is provided a condensed heterocyclic derivative represented by formula [I]:

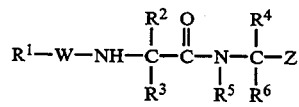

wherein $R^1$ represents a lower alkyl group optionally having at least one substituent selected from the group consisting of a halogen atom, a cyano group, and a methoxy group, an alkenyl group, an alkynyl group, a cycloalkyl group optionally having at least one methyl group, a cycloalkenyl group optionally having at least one methyl group, a cyclic ether group optionally having at least one methyl group, an aralkyl group optionally having at least one substituent selected from the group consisting of a methyl group, a methoxy group, and a nitro group, a phenyl group optionally having at least one substituent selected from the group consisting of a halogen atom, a methyl group, a methoxy group, a nitro group, and a methoxycarbonyl group, a dimethylamino group, or an ethoxy carbonyl group, $R^2$, $R^3$, $R^4$, $R^5$, and $R^6$ independently represent a hydrogen atom, a lower alkyl group optionally having at least one halogen group, a cycloalkyl group, an aralkyl group; a phenyl group, a cyano group, an acyl group, a lower alkoxy group, or a lower alkoxycarbonyl group, $R^2$ may form an alkylic ring having 3 to 6 carbon atoms with $R^3$;

Z is represented by the following formulae:

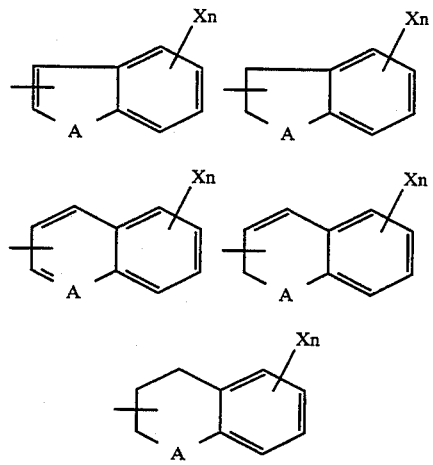

wherein X represents a hydrogen atom, a halogen atom, an alkyl group optionally having at least one halogen atom, an alkynyl group, a methoxy group, a trifluoromethoxy group, a hydroxyl group, a methoxycarbonyl group, a methylcarbonyloxy group, an amino group, a dimethylamino group, a nitro group, a methylthio group, a methylsulfinyl group, a methylsulfonyl group, a phenyl group, an acetyl group, a formyl group, or a cyano group; n is an integer of 1, 2, or 3;

A is O, S, N, or represented by the formula:

wherein $R^7$ represents a hydrogen atom, a methyl group, an acetyl group, or a benzoyl group; and W is represented by —C(O)—, —$SO_2$—, —NHC(O)—, —N($CH_3$)C(O)—, —OC(O)—, —SC(O)—, —OC(S)—, or —SC(S)—.

According to a second aspect of the present invention, there is provided an agricultural or horticultural fungicide containing the condensed heterocyclic derivative described above as the active ingredient.

In the present specification, the term "lower" is used herein to mean possessing at most 6 carbon atoms. The term "alkyl group" is used herein to mean a straight or branched alkyl group possessing 1 to 15 carbon atoms including, but not limited to, a methyl group, ethyl group, n-propyl group, isopropyl group, n-butyl group, isobutyl group, sec-butyl group, t-butyl group, n-pentyl group, 1-methylbutyl group, 2-methylbutyl group, 3-methylbutyl group, 2,2-dimethylpropyl group, 1,1-dimethylpropyl group, 1-ethylpropyl group, n-hexyl group, n-heptyl group, n-octyl group, n-nonyl group, n-decyl group, n-undecyl group, n-dodecyl group, n-tridecyl group, n-tetradecyl group, n-pentadecyl group, or the like.

A lower alkyl group optionally having at least one substituent selected from the group consisting of a halogen atom, a cyano group, and a methoxy group includes, for example, a monochloroethyl group, trifluoroethyl group, 1-cyanoethyl group, 1-cyano-1-methylethyl group, 1-methoxy-1-trifluoromethylbutyl group, perfluoro-tert-butyl group or the like.

The term "halogen" is used herein to mean a fluorine atom, chlorine atom, bromine atom, iodine atom, or the like. The term "alkenyl group" is used herein to mean a straight or branched alkenyl group possessing 2 to 6 carbon atoms and including, but not limited to, a vinyl group, 1-propenyl group, 2-propenyl group, isopropenyl group, 1-butenyl group, 2-butenyl group, 3-butenyl group, 1-methyl-1-propenyl group, 2-methylpropenyl group, 1-ethylvinyl group, 2-pentenyl group, 2-hexenyl group, or the like. The term "alkynyl group" is used herein to mean a straight or branched alkynyl group possessing 2 to 6 carbon atoms and including, for example, an ethynyl group, propynyl group, butynyl group, 1-methyl-2-propynyl group, 2-pentynyl group, 2-hexynyl or the like.

The term "cycloalkyl group" is used herein to mean a cycloalkyl group possessing 3 to 8 carbon atoms and including, but not limited to, a cyclopropyl group, cyclobutyl group, cyclopentyl group, cyclohexyl group, cycloheptyl group, cyclooctyl group, or the like.

A cycloalkyl group optionally having at least one methyl group includes, for example, a 1-methylcyclopropyl group, 2-methylcyclopropyl group, 1-methylcyclobutyl group, 2-methylcyclobutyl group, 1,2-dimethylcyclobutyl group, 1-methylcyclopentyl group, 2-methylcyclopentyl group, 3-methylcyclopentyl group, 1,2-dimethylcyclopentyl group, 1,2,3-trimethylcyclopentyl group, or the like.

The term "cycloalkenyl" is used herein to mean a cycloalkenyl group possessing 3 to 8 carbon atoms and including, but not limited to, a 1-cyclopropenyl group, 2-cyclopropenyl group, 1-cyclobutenyl group, 2-cyclobutenyl group, 1-cyclopentenyl group, 2-cyclopentenyl group, 3-cyclopentenyl group, 1-cyclohexenyl group, 2-cyclohexenyl group, 3-cyclohexenyl group, 1-cycloheptenyl group, 2-cycloheptenyl group, 3-cycloheptenyl group, 4-cycloheptenyl group, 1-cyclooctenyl group, 2-cyclooctenyl group, 3-cyclooctenyl group, 4-cyclooctenyl group, or the like.

A cycloalkenyl group optionally having at least one methyl group includes, for example, a 1-methyl-2-cyclopentenyl group, 2-methyl-1-cyclopentenyl group, 3-methyl-1-cyclopentenyl group, 3,4-dimethyl-1-cyclopentenyl group, 1-methyl-2-cyclohexenyl group, 4-methyl-1-cyclohexenyl group, 1,2,5-trimethyl-3-cyclohexenyl group, or the like.

The term "aralkyl" is used herein to mean an aralkyl group possessing 7 to 10 carbon atoms and including, but not limited to, a benzyl group, phenethyl group, or the like.

An aralkyl group optionally having at least one substituent selected from the group consisting of a methyl group, a methoxy group, and a nitro group, includes, for example, a 4-methylbenzyl group, α-methylbenzyl group, 4-methoxybenzyl group, 4-nitrobenzyl group, 2,4-dimethylbenzyl group, 2-methyl-3-methoxy-4-nitrobenzyl group, α-methyl-4-methylphenethyl group or the like.

The term "cyclic ether group" is used herein to mean a cyclic ether group possessing 2 to 6 carbon atoms and including, for example, an oxiranyl group, 2-oxetanyl group, 3-tetrahydrofuryl group, 2-tetrahydropyranyl group, or the like.

A cyclic ether group optionally having at least one methyl group includes, for example, 2-methyloxiranyl, 2-methyl-3-tetrahydrofuryl group, 2,4-dimethyl-3-tetrahydrofuryl group, 2,4,5-trimethyl-3-tetrahydrofuryl group, or the like.

An acyl group includes an acetyl group, benzoyl group, or the like.

A phenyl group optionally having at least one substituent selected from the group consisting of a halogen atom, a methyl group, a methoxy group, a nitro group, and a methoxycarbonyl group includes, for example, a 2-chlorophenyl group, 3-methylphenyl group, 4-methoxyphenyl group, 4-nitrophenyl group, 4-methoxycarbonylphenyl group, 2-methoxy-4-nitrophenyl group, perfluorophenyl group or the like.

The preferred compounds of this invention consist of the compounds represented by formula (I), wherein $R^1$ represents a straight or branched alkyl group possessing 2 to 6 carbon atoms, a straight or branched alkenyl group possessing 3 carbon atoms, a cycloalkyl group possessing 5 to 6 carbon atoms, or a non-substituted phenyl group; $R^2$ represents a hydrogen atom; $R^3$ represents an isopropyl group; $R^4$ represents a hydrogen atom, a phenyl group, a methyl group, or an ethyl group; $R^5$ represents a hydrogen atom or a methyl group; $R^6$ represents a hydrogen atom; W is represented by —OC(O)—; Z represents a substituted heterocyclic group including a benzofuran group, a benzothiophene group, an indole group, a 2,3-dihydrobenzofuran group having one or two (same or different) substituent such as a hydrogen atom, a fluorine atom, a chlorine atom, a nitro group, a cyano group, or a methyl group; and the amino acid is an L-isomer.

The compounds represented by formula [I] according to the present invention can exist in stereoisomers by venue of the presence of two or more chiral centers. The present invention contemplate all such stereoisomers, including diastereomers, enantiomers, and mixtures thereof, which can be separated by appropriate methods.

Next, the compounds represented by formula [I] according to the present invention are listed in Tables 1 to 7. However, it should be understood that the invention is not limited to these compounds. The compound Nos. given in Tables 1 to 7 will be referred to in the subsequent description.

In Tables 1 to 7, Compound Nos. 1, 2, and 3; Compound Nos. 68, 69, and 303; Compound Nos. 70, 71, and 296; Compound Nos. 129, 130, and 131; Compound Nos. 136, 137, and 138; Compound Nos. 108, 375, and 109; Compound Nos. 382, 23, and 24; Compound Nos. 376, 163, and 164; and Compound Nos. 377, 378, and 379 are a mixture of diastereomers, and are also individual diastereomers. In addition, Compound Nos. 16 and 17; Compound Nos. 97 and 98; Compound Nos. 102 and 103; Compound Nos. 115 and 327; Compound Nos. 132 and 133; Compound Nos. 227 and 362; Compound Nos. 228 and 364; Compound Nos. 230 and 365; Compound Nos. 233 and 363; Compound Nos. 336 and 337; Compound Nos. 405 and 406; and Compound Nos. 423 and 424 are a mixture of diastereomers, and are also one of the individual diastereomers, respectively. Compound Nos. 161 and 162 are the individual diastereomers.

TABLE 1

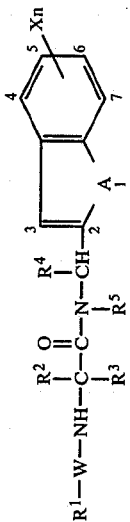

| Compound No. | R¹ | R² | R³ | R⁴ | R⁵ | W | Xn | A | Amino Acid Isomer | Melting Point (°C.) or Refractive Index ($n_D^{20}$) |
|---|---|---|---|---|---|---|---|---|---|---|
| 1 | t-C₄H₉ | H | i-C₃H₇ | CH₃ | H | OC(O) | H | O | L | 92–96 |
| 2 | t-C₄H₉ | H | i-C₃H₇ | CH₃ | H | OC(O) | H | O | L | 88–90 |
| 3 | t-C₄H₉ | H | i-C₃H₇ | CH₃ | H | OC(O) | H | O | L | 124–126 |
| 4 | t-C₄H₉ | H | i-C₃H₇ | CH₃ | H | OC(O) | 5,7-Cl₂ | O | L | 123–125 |
| 5 | t-C₄H₉ | H | i-C₃H₇ | CH₃ | H | OC(O) | 5-OCH₃ | O | L | 94–96 |
| 6 | t-C₄H₉ | H | i-C₃H₇ | CH₃ | H | OC(O) | 5-CH₃ | O | L | 103–106 |
| 7 | t-C₄H₉ | H | i-C₃H₇ | CH₃ | H | OC(O) | 4-Cl | O | L | 53–54 |
| 8 | t-C₄H₉ | H | i-C₃H₇ | CH₃ | H | OC(O) | 5-NH₂ | O | L | 71–72 |
| 9 | t-C₄H₉ | H | i-C₃H₇ | CH₃ | H | OC(O) | 5-N(CH₃)₂ | O | L | 128–132 |
| 10 | t-C₄H₉ | H | i-C₃H₇ | CH₃ | H | OC(O) | 5-CO₂CH₃ | O | L | 135–137 |
| 11 | t-C₄H₉ | H | i-C₃H₇ | CH₃ | H | OC(O) | 6-Cl | O | L | 58–59 |
| 12 | t-C₄H₉ | H | i-C₃H₇ | CH₃ | H | OC(O) | 7-Cl | O | L | 94–97 |
| 13 | t-C₄H₉ | H | i-C₃H₇ | CH₃ | H | OC(O) | 5-Cl | O | DL | 154–159 |
| 14 | t-C₄H₉ | H | i-C₃H₇ | CH₃ | H | OC(O) | 6-CH₃ | O | L | 120–125 |
| 15 | t-C₄H₉ | H | i-C₃H₇ | CH₃ | H | OC(O) | 7-CH₃ | O | L | 60–65 |
| 16 | t-C₄H₉ | H | i-C₃H₇ | CH₃ | H | OC(O) | 5-CN | O | L | 124–128 |
| 17 | t-C₄H₉ | H | i-C₃H₇ | CH₃ | H | OC(O) | 6-CN | O | L | 123–124 |
| 18 | t-C₄H₉ | H | i-C₃H₇ | CH₃ | H | OC(O) | 4-CH₃ | O | L | 76–80 |
| 19 | t-C₄H₉ | H | i-C₃H₇ | CH₃ | H | OC(O) | 5-OCF₃ | O | L | 65–70 |
| 20 | t-C₄H₉ | H | i-C₃H₇ | CH₃ | H | OC(O) | 5-SCH₃ | O | L | 103–108 |
| 21 | t-C₄H₉ | H | i-C₃H₇ | CH₃ | H | OC(O) | 5-SOCH₃ | O | L | 80–83 |
| 22 | t-C₄H₉ | H | i-C₃H₇ | CH₃ | H | OC(O) | 5-SO₂CH₃ | O | L | 80–82 |
| 23 | t-C₄H₉ | H | i-C₃H₇ | CH₃ | H | OC(O) | 5-NO₂ | O | L | 115–116 |
| 24 | t-C₄H₉ | H | i-C₃H₇ | CH₃ | H | OC(O) | 6-NO₂ | O | L | 173–175 |
| 25 | t-C₄H₉ | H | i-C₃H₇ | CH₃ | H | OC(O) | 5-NO₂ | O | DL | 152–158 |
| 26 | t-C₄H₉ | H | i-C₃H₇ | CH₃ | H | OC(O) | 5-Cl | O | D | 118–122 |
| 27 | t-C₄H₉ | H | i-C₃H₇ | CH₃ | H | OC(O) | 5-C₂H₅ | O | L | 119–122 |
| 28 | t-C₄H₉ | H | i-C₃H₇ | CH₃ | H | OC(O) | 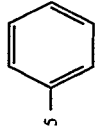 5 | O | L | 98–101 |
| 29 | t-C₄H₉ | H | i-C₃H₇ | CH₃ | H | OC(O) | 5,6-Cl₂ | O | L | 68–70 |
| 30 | t-C₄H₉ | H | i-C₃H₇ | CH₃ | H | OC(O) | 3-CH₃ | O | L | 54–55 |
| 31 | t-C₄H₉ | H | i-C₃H₇ | CH₃ | H | OC(O) | 3-CH₃, 5-Cl | O | L | 134–136 |
| 32 | t-C₄H₉ | H | i-C₃H₇ | CH₃ | H | OC(O) | 3-Cl | O | L | 53–56 |
| 33 | t-C₄H₉ | H | i-C₃H₇ | CH₃ | H | OC(O) | 4-CH₃, 5-Cl | O | L | 120–127 |
| 34 | t-C₄H₉ | H | i-C₃H₇ | CH₃ | H | OC(O) | 5-CHO | O | L | |
| 35 | t-C₄H₉ | H | i-C₃H₇ | CH₃ | H | OC(O) | 5-C≡CH | O | L | |
| 36 | t-C₄H₉ | H | i-C₃H₇ | CH₃ | H | OC(O) | 5-CH₂F | O | L | |

| No. | | | | | | | | | | |
|---|---|---|---|---|---|---|---|---|---|---|
| | | | | | | | -continued | | | |
| 37 | t-C4H9 | H | i-C3H7 | CH3 | H | OC(O) | 5-COCH3 | O | L | |
| 38 | t-C4H9 | H | i-C3H7 | CH3 | H | OC(O) | 5-OCOCH3 | O | L | |
| 39 | t-C4H9 | H | i-C3H7 | CH3 | H | OC(O) | 5-OH | O | L | |
| 40 | t-C4H9 | H | i-C3H7 | CH3 | H | OC(O) | 5-n-C5H11 | O | L | 1.5114 |
| 41 | t-C4H9 | H | i-C3H7 | CH3 | H | OC(O) | 5-n-C4H9 | O | L | |
| 42 | t-C4H9 | H | i-C3H7 | CH3 | H | OC(O) | (C6H5)3 | O | L | |
| 43 | t-C4H9 | H | i-C3H7 | CH3 | H | OC(O) | 3,5-Cl2 | O | L | 158-162 |
| 44 | t-C4H9 | H | i-C3H7 | CH3 | H | OC(O) | 3-Cl, 5-NO2 | O | L | 150-155 |
| 45 | t-C4H9 | H | i-C3H7 | CH3 | H | OC(O) | 4-Cl, 5-NO2 | O | L | |
| 46 | t-C4H9 | H | i-C3H7 | CH3 | H | OC(O) | 5-NO2, 6-Cl | O | L | 165-170 |
| 47 | t-C4H9 | H | i-C3H7 | CH3 | H | OC(O) | 5-NO2, 7-Cl | O | L | |
| 48 | t-C4H9 | H | i-C3H7 | CH3 | H | OC(O) | 3-CH3, 5-NO2 | O | L | |
| 49 | t-C4H9 | H | i-C3H7 | CH3 | H | OC(O) | 4-CH3, 5-NO2 | O | L | |
| 50 | t-C4H9 | H | i-C3H7 | CH3 | H | OC(O) | 5-NO2, 6-CH3 | O | L | |
| 51 | t-C4H9 | H | i-C3H7 | CH3 | H | OC(O) | 5-NO2, 7-CH3 | O | L | |
| 52 | t-C4H9 | H | i-C3H7 | CH3 | H | OC(O) | 5,7-(NO2)2 | O | L | |
| 53 | t-C4H9 | H | i-C3H7 | CH3 | H | OC(O) | 5,6-(CN)2 | O | L | |
| 54 | C2H5 | H | i-C3H7 | CH3 | H | OC(O) | 5,6,7-Cl3 | O | L | |
| 55 | CH2=CHCH2 | H | i-C3H7 | CH3 | H | OC(O) | 5-Cl | O | L | |
| 56 | | H | i-C3H7 | CH3 | H | OC(O) | 5-Cl | O | L | |
| 57 | C6H5CH2— | H | i-C3H7 | CH3 | H | OC(O) | 5-Cl | O | L | 162-168 |
| 58 | n-C3H7 | H | i-C3H7 | CH3 | H | OC(O) | 5-Cl | O | L | 156-160 |
| 59 | n-C4H9 | H | i-C3H7 | CH3 | H | OC(O) | 5-Cl | O | L | 158-161 |
| 60 | i-C4H9 | H | i-C3H7 | CH3 | H | OC(O) | 5-Cl | O | L | 141-145 |
| 61 | n-C5H11 | H | i-C3H7 | CH3 | H | OC(O) | 5-Cl | O | L | 115-118 |
| 62 | n-C6H13 | H | i-C3H7 | CH3 | H | OC(O) | 5-Cl | O | L | 177-183 |
| 63 | ClCH2CH2 | H | i-C3H7 | CH3 | H | OC(O) | 5-Cl | O | L | 130-133 |
| 64 | Cl3CCH2 | H | i-C3H7 | CH3 | H | OC(O) | 5-Cl | O | L | 149-153 |
| 65 | CH3 | H | i-C3H7 | CH3 | H | OC(O) | 5-Cl | O | L | 151-153 |
| 66 | CH3OCH2CH2 | H | i-C3H7 | CH3 | H | OC(O) | 5-Cl | O | L | |
| 67 | cyclohexyl | H | i-C3H7 | CH3 | H | OC(O) | 5-Cl | O | L | 190-196 |
| 68 | methylcyclopentyl | H | i-C3H7 | CH3 | H | OC(O) | 5-Cl | O | L | 175-179 |

-continued

| | | | | | | | | |
|---|---|---|---|---|---|---|---|---|
| 69 | cyclopentyl | H | i-C$_3$H$_7$ | CH$_3$ | H | OC(O) | 5-Cl | O | 177-178 | L |
| 70 | i-C$_3$H$_7$ | H | i-C$_3$H$_7$ | CH$_3$ | H | OC(O) | 5-Cl | O | 167-169 | L |
| 71 | i-C$_3$H$_7$ | H | i-C$_3$H$_7$ | CH$_3$ | H | OC(O) | 5-Cl | O | 184-186 | L |
| 72 | CH$_2$=C(CH$_3$)— | H | i-C$_3$H$_7$ | CH$_3$ | H | OC(O) | 5-Cl | O | 166-170 | L |
| 73 | CH$_2$=CH— | H | i-C$_3$H$_7$ | CH$_3$ | H | OC(O) | 5-Cl | O | 176-181 | L |
| 74 | 4-NO$_2$-C$_6$H$_4$-CH$_2$— | H | i-C$_3$H$_7$ | CH$_3$ | H | OC(O) | 5-Cl | O | 131-135 | L |
| 75 | 4-CH$_3$-C$_6$H$_4$-CH$_2$— | H | i-C$_3$H$_7$ | CH$_3$ | H | OC(O) | 5-Cl | O | 173-178 | L |
| 76 | s-C$_4$H$_9$ | H | i-C$_3$H$_7$ | CH$_3$ | H | OC(O) | 5-Cl | O | 153-158 | L |
| 77 | CH≡CCH$_2$— | H | i-C$_3$H$_7$ | CH$_3$ | H | OC(O) | 5-Cl | O | 178-180 | L |
| 78 | CF$_3$CH$_2$— | H | i-C$_3$H$_7$ | CH$_3$ | H | OC(O) | 5-Cl | O | 208-209 | L |
| 79 | C$_2$H$_5$(CH$_3$)$_2$C— | H | i-C$_3$H$_7$ | CH$_3$ | H | OC(O) | 5-Cl | O | 53-55 | L |
| 80 | cyclobutyl | H | i-C$_3$H$_7$ | CH$_3$ | H | OC(O) | 5-Cl | O | 170-175 | L |
| 81 | cyclopropyl | H | i-C$_3$H$_7$ | CH$_3$ | H | OC(O) | 5-Cl | O | | L |
| 82 | 1-methylcyclopentyl | H | i-C$_3$H$_7$ | CH$_3$ | H | OC(O) | 5-Cl | O | | L |
| 83 | (C$_2$H$_5$)$_2$CH | H | i-C$_3$H$_7$ | CH$_3$ | H | OC(O) | 5-Cl | O | 149-151 | L |
| 84 | (CF$_3$)$_3$C | H | i-C$_3$H$_7$ | CH$_3$ | H | OC(O) | 5-Cl | O | | L |
| 85 | CF$_3$(CH$_3$)$_2$C | H | i-C$_3$H$_7$ | CH$_3$ | H | OC(O) | 5-Cl | O | 63-66 | L |
| 86 | ClCH$_2$— | H | i-C$_3$H$_7$ | CH$_3$ | H | OC(O) | 5-Cl | O | 167-169 | L |
| 87 | Cl(CH$_3$)CH— | H | i-C$_3$H$_7$ | CH$_3$ | H | OC(O) | 5-Cl | O | | L |
| 88 | glycidyl (CH$_2$—CH—O) | H | i-C$_3$H$_7$ | CH$_3$ | H | OC(O) | 5-Cl | O | | L |

-continued

| Structure | | | | | | | | | |
|---|---|---|---|---|---|---|---|---|---|
| CH₃-C(CH₃)(CH₂)O (epoxide) | H | i-C₃H₇ | CH₃ | H | OC(O) | 5-Cl | O | L | |
| 2-Cl-C₆H₄ | H | i-C₃H₇ | CH₃ | H | OC(O) | 5-Cl | O | L | 147–152 |
| 3-Cl-C₆H₄ | H | i-C₃H₇ | CH₃ | H | OC(O) | 5-Cl | O | L | 163–166 |
| 4-CH₃O-C₆H₄ | H | i-C₃H₇ | CH₃ | H | OC(O) | 5-Cl | O | L | 174–179 |
| 4-F-C₆H₄ | H | i-C₃H₇ | CH₃ | H | OC(O) | 5-Cl | O | L | 176–180 |
| 4-Br-C₆H₄ | H | i-C₃H₇ | CH₃ | H | OC(O) | 5-Cl | O | L | 198–203 |
| 4-CH₃O₂C-C₆H₄ | H | i-C₃H₇ | CH₃ | H | OC(O) | 5-Cl | O | L | |
| 4-NO₂-C₆H₄ | H | i-C₃H₇ | CH₃ | H | OC(O) | 5-Cl | O | L | 148–152 |

Compound numbers: 89, 90, 91, 92, 93, 94, 95, 96

-continued
| | | | | | | | | |
|---|---|---|---|---|---|---|---|---|
| 97 | 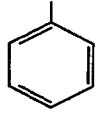 | i-C₃H₇ | CH₃ | H | OC(O) | 5-NO₂ | O | L | 195–199 |
| 98 | 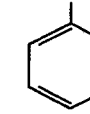 | i-C₃H₇ | CH₃ | H | OC(O) | 5-NO₂ | O | L | |
| 99 | 4-Cl-C₆H₄ | i-C₃H₇ | CH₃ | H | OC(O) | 5-NO₂ | O | L | 184–188 |
| 100 | 4-CH₃-C₆H₄ | i-C₃H₇ | CH₃ | H | OC(O) | 5-NO₂ | O | L | 174–179 |
| 101 | C₂H₅ | i-C₃H₇ | CH₃ | H | OC(O) | 5-CN | O | L | 190–191 |
| 102 | i-C₃H₇ | i-C₃H₇ | CH₃ | H | OC(O) | 5-CN | O | L | 191–193 |
| 103 | i-C₃H₇ | i-C₃H₇ | CH₃ | H | OC(O) | 5-CN | O | L | |
| 104 | 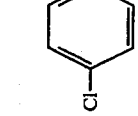 | i-C₃H₇ | CH₃ | H | OC(O) | 5-CN | O | L | 181–184 |
| 105 | cyclopentyl | i-C₃H₇ | CH₃ | H | OC(O) | 5-CN | O | L | 151–155 |
| 106 | cyclohexyl | i-C₃H₇ | CH₃ | H | OC(O) | 5-CN | O | L | 188–190 |
| 107 | s-C₄H₉ | i-C₃H₇ | CH₃ | H | OC(O) | 5-CN | O | L | 181–183 |
| 108 | i-C₃H₇ | i-C₃H₇ | CH₃ | H | OC(O) | 5-NO₂ | O | L | 189–195 |
| 109 | i-C₃H₇ | i-C₃H₇ | CH₃ | H | OC(O) | 5-NO₂ | O | L | 187–188 |

-continued

| No. | Structure | | | | | | | mp |
|---|---|---|---|---|---|---|---|---|
| 110 | 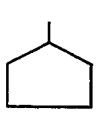 | H | i-$C_3H_7$ | $CH_3$ | H | OC(O) | 5-$NO_2$ | O | L | 196–201 |
| 111 | 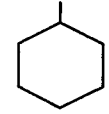 | H | i-$C_3H_7$ | $CH_3$ | H | OC(O) | 5-$NO_2$ | O | L | 193–198 |
| 112 | s-$C_4H_9$ | H | i-$C_3H_7$ | $CH_3$ | H | OC(O) | 5-$NO_2$ | O | L | 178–183 |
| 113 | 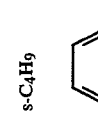 | H | i-$C_3H_7$ | $CH_3$ | H | OC(O) | 5-$NO_2$ | O | L | |
| 114 | $C_2H_5$ | H | i-$C_3H_7$ | $CH_3$ | H | OC(O) | 5-F | O | L | 155–160 |
| 115 | i-$C_3H_7$ | H | i-$C_3H_7$ | $CH_3$ | H | OC(O) | 5-F | O | L | 164–166 |
| 116 | 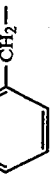 | H | i-$C_3H_7$ | $CH_3$ | H | OC(O) | 5-F | O | L | 169–173 |
| 117 | 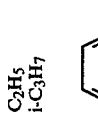 | H | i-$C_3H_7$ | $CH_3$ | H | OC(O) | 5-F | O | L | 165–170 |
| 118 | 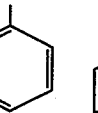 | H | i-$C_3H_7$ | $CH_3$ | H | OC(O) | 5-F | O | L | 175–178 |
| 119 | s-$C_4H_9$ | H | i-$C_3H_7$ | $CH_3$ | H | OC(O) | H | O | L | 130–133 |
| 120 | i-$C_3H_7$ | H | i-$C_3H_7$ | $CH_3$ | H | OC(O) | H | O | L | 122–125 |
| 121 | 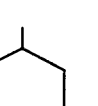 | H | i-$C_3H_7$ | $CH_3$ | H | OC(O) | H | O | L | 173–177 |
| 122 | t-$C_4H_9$ | H | H | $CH_3$ | H | OC(O) | 5-Cl | O | — | 103–104 |
| 123 | t-$C_4H_9$ | H | $CH_3$ | $CH_3$ | H | OC(O) | 5-Cl | O | L | 95–99 |

| No. | | | | | | | | | mp |
|---|---|---|---|---|---|---|---|---|---|
| 124 | t-C$_4$H$_9$ | H | C$_6$H$_5$CH$_2$— | CH$_3$ | H | OC(O) | 5-Cl | O | L | 130–136 |
| 125 | t-C$_4$H$_9$ | H | s-C$_4$H$_9$ | CH$_3$ | H | OC(O) | 5-Cl | O | L | 136–140 |
| 126 | t-C$_4$H$_9$ | H | —(CH$_2$)$_4$— | CH$_3$ | H | OC(O) | 5-Cl | O | — | 193–195 |
| 127 | t-C$_4$H$_9$ | H | —(CH$_2$)$_5$— | CH$_3$ | H | OC(O) | 5-Cl | O | — | 219–222 |
| 128 | t-C$_4$H$_9$ | H | C$_2$H$_5$ | CH$_3$ | H | OC(O) | 5-Cl | O | L | 106–112 |
| 129 | t-C$_4$H$_9$ | H | i-C$_4$H$_9$ | CH$_3$ | H | OC(O) | 5-Cl | O | L | 56–58 |
| 130 | t-C$_4$H$_9$ | H | i-C$_4$H$_9$ | CH$_3$ | H | OC(O) | 5-Cl | O | L | 125–126 |
| 131 | t-C$_4$H$_9$ | H | i-C$_4$H$_9$ | CH$_3$ | H | OC(O) | 5-Cl | O | L | 142–144 |
| 132 | t-C$_4$H$_9$ | H | C$_6$H$_5$ (cyclohexyl) | CH$_3$ | H | OC(O) | 5-Cl | O | L | 71–75 |
| 133 | t-C$_4$H$_9$ | H | C$_6$H$_5$ (cyclohexyl) | CH$_3$ | H | OC(O) | 5-Cl | O | L | 130–132 |
| 134 | t-C$_4$H$_9$ | H | n-C$_3$H$_7$ | CH$_3$ | H | OC(O) | 5-Cl | O | L | 105–111 |
| 135 | t-C$_4$H$_9$ | H | n-C$_4$H$_9$ | CH$_3$ | H | OC(O) | 5-Cl | O | L | 93–98 |
| 136 | t-C$_4$H$_9$ | H | t-C$_4$H$_9$ | CH$_3$ | H | OC(O) | 5-Cl | O | L | 124–129 |
| 137 | t-C$_4$H$_9$ | H | i-C$_4$H$_9$ | CH$_3$ | H | OC(O) | 5-Cl | O | L | 164–165 |
| 138 | t-C$_4$H$_9$ | H | i-C$_4$H$_9$ | CH$_3$ | H | OC(O) | 5-Cl | O | L | 137–139 |
| 139 | t-C$_4$H$_9$ | H | cyclopentyl | CH$_3$ | H | OC(O) | 5-Cl | O | DL | 176–178 |
| 140 | t-C$_4$H$_9$ | H | i-C$_3$H$_7$, CH$_3$ | CH$_3$ | H | OC(O) | 5-Cl | O | DL | 169–173 |
| 141 | t-C$_4$H$_9$ | H | —(CH$_2$)$_2$— | CH$_3$ | H | OC(O) | 5-Cl | O | — | 59–61 |
| 142 | t-C$_4$H$_9$ | H | CF$_3$CH(CH$_3$)— | CH$_3$ | H | OC(O) | 5-Cl | O | DL | 159–163 |
| 143 | 4-Cl-C$_6$H$_4$ | H | i-C$_3$H$_7$ | CH$_3$ | H | CO | 5-Cl | O | L | 206–209 |
| 144 | CH$_3$ | h | i-C$_3$H$_7$ | CH$_3$ | H | CO | 5-Cl | O | L | 219–222 |
| 145 | t-C$_4$H$_9$ | H | i-C$_3$H$_7$ | CH$_3$ | H | CO | 5-Cl | O | L | 74–75 |

|  |  |  |  |  | -continued |  |  |  |
|---|---|---|---|---|---|---|---|---|
| 146 | CF₃ | i-C₃H₇ | CH₃ | H | CO | 5-Cl | O | L | 132-138 |
| 147 | C₂H₅OC(O) | i-C₃H₇ | CH₃ | H | CO | 5-Cl | O | L | 75-76 |
| 148 | 4-Cl-C₆H₄ | i-C₃H₇ | CH₃ | H | SO2 | 5-Cl | O | L | 149-153 |
| 149 | CH₃ | i-C₃H₇ | CH₃ | H | SO2 | 5-Cl | O | L | 172-177 |
| 150 | CH₃ | i-C₃H₇ | CH₃ | H | NC(O)—CH₃ | 5-Cl | O | L | 146-151 |
| 151 | C₆H₅ | i-C₃H₇ | CH₃ | H | NC(O)—CH₃ | 5-Cl | O | L | not determined |
| 152 | (CH₃)₂N— | i-C₃H₇ | CH₃ | H | SO2 | 5-Cl | O | L | 126-130 |
| 153 | 4-Cl-C₆H₄ | i-C₃H₇ | CH₃ | H | NCH(O) | 5-Cl | O | L | 255-258 |
| 154 | C₂H₅— | i-C₃H₇ | CH₃ | H | SC(O) | 5-Cl | O | L | 163-169 |
| 155 | C₆H₅ | i-C₃H₇ | CH₃ | H | SC(O) | 5-Cl | O | L | 181-186 |
| 156 | C₆H₅ | i-C₃H₇ | CH₃ | H | OC(S) | 5-Cl | O | L | 64-68 |
| 157 | t-C₄H₉ | i-C₃H₇ | CH₃ | H | OC(O) | H | S | L | 54-57 |
| 158 | t-C₄H₉ | i-C₃H₇ | CH₃ | H | OC(O) | 5-NO₂ | S | L | 120-121 |
| 159 | t-C₄H₉ | i-C₃H₇ | CH₃ | H | OC(O) | 3-CH₃ | S | L | 138-140 |
| 160 | t-C₄H₉ | i-C₃H₇ | CH₃ | H | OC(O) | 3-CH₃, 5-Cl | S | L | 150-152 |
| 161 | C₂H₅ | i-C₃H₇ | CH₃ | H | OC(O) | H | S | L | 179-180 |
| 162 | C₂H₅ | i-C₃H₇ | CH₃ | H | OC(O) | H | S | L | 204-206 |
| 163 | i-C₃H₇ | i-C₃H₇ | CH₃ | H | OC(O) | H | S | L | 186-188 |
| 164 | i-C₃H₇ | i-C₃H₇ | CH₃ | H | OC(O) | H | S | L | 203-205 |

-continued

| No. | | | | | | | |
|---|---|---|---|---|---|---|---|
| 165 | 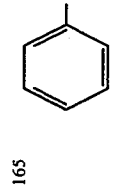 | H | i-C3H7 | CH3 | H | OC(O) | H | S | 178-180 |
| 166 | t-C4H9 | H | i-C3H7 | CH3 | H | OC(O) | 3-Cl | S | 69-71 |
| 167 | t-C4H9 | H | i-C3H7 | CH3 | H | OC(O) | 4-Cl | S | 1.5306 |
| 168 | t-C4H9 | H | i-C3H7 | CH3 | H | OC(O) | 7-Cl | S | 1.5295 |
| 169 | t-C4H9 | H | i-C3H7 | C2H5 | H | OC(O) | 5-Cl | O | 109-115 |
| 170 | t-C4H9 | H | i-C3H7 | CH3 | H | OC(O) | 5-Cl | O | 126-132 |
| 171 | t-C4H9 | H | i-C3H7 | H | H | OC(O) | 5-Cl | O | 135-138 |
| 172 | t-C4H9 | H | i-C3H7 | CN | H | OC(O) | H | O | 135-141 |
| 173 | t-C4H9 | H | i-C3H7 | CH3 | CH3 | OC(O) | 5-Cl | O | |
| 174 | t-C4H9 | H | i-C3H7 | CH3 | i-C3H7 | OC(O) | 5-Cl | O | |
| 175 | t-C4H9 | H | i-C3H7 | CN | H | OC(O) | 3-CH3 | S | |
| 176 | C2H5 | H | i-C3H7 | CH3 | H | OC(O) | 3-CH3 | S | 182-184 |
| 177 | i-C3H7 | H | i-C3H7 | CH3 | H | OC(O) | 3-CH3 | S | 182-184 |
| 178 | 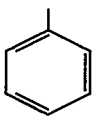 | H | i-C3H7 | CH3 | H | OC(O) | 3-CH3 | S | 184-185 |
| 179 | t-C4H9 | H | i-C3H7 | H | H | OC(O) | H | S | 129-130 |
| 180 | t-C4H9 | H | i-C3H7 | CH3 | H | OC(O) | 5-F | S | 50-54 |
| 181 | t-C4H9 | H | i-C3H7 | CH3 | H | OC(O) | 5-Cl | S | 149 ∝ 156 |
| 182 | t-C4H9 | H | i-C3H7 | CH3 | H | OC(O) | 5-Br | S | 139-145 |
| 183 | t-C4H9 | H | i-C3H7 | CH3 | H | OC(O) | 5-CN | S | |
| 184 | t-C4H9 | H | i-C3H7 | CH3 | H | OC(O) | 5-CH3 | S | |
| 185 | t-C4H9 | H | i-C3H7 | CH3 | H | OC(O) | 5-OCH3 | S | |
| 186 | t-C4H9 | H | i-C3H7 | CH3 | H | OC(O) | 5-CF3 | S | |
| 187 | t-C4H9 | H | i-C3H7 | CH3 | H | OC(O) | 4-CH3 | S | |
| 188 | t-C4H9 | H | i-C3H7 | CH3 | H | OC(O) | 6-CH3 | S | 90-94 |
| 189 | t-C4H9 | H | i-C3H7 | CH3 | H | OC(O) | 4,7-Cl2 | S | |
| 190 | t-C4H9 | H | i-C3H7 | CH3 | H | OC(O) | 5,7-Cl2 | S | |
| 191 | t-C4H9 | H | i-C3H7 | CH3 | H | OC(O) | 3-OCH3 | S | |
| 192 | i-C3H7 | H | i-C3H7 | CH3 | H | OC(O) | 5-F | S | 135-139 |
| 193 | i-C3H7 | H | i-C3H7 | CH3 | H | OC(O) | 5-Cl | S | 181-184 |
| 194 | i-C3H7 | H | i-C3H7 | CH3 | H | OC(O) | 5-Br | S | 170-173 |
| 195 | i-C3H7 | H | i-C3H7 | CH3 | H | OC(O) | 5-CN | S | |
| 196 | i-C3H7 | H | i-C3H7 | CH3 | H | OC(O) | 5-CH3 | S | |
| 197 | i-C3H7 | H | i-C3H7 | CH3 | H | OC(O) | 5-OCH3 | S | |
| 198 | i-C3H7 | H | i-C3H7 | CH3 | H | OC(O) | 5-CF3 | S | 170-175 |
| 199 | i-C3H7 | H | i-C3H7 | CH3 | H | OC(O) | 4-CH3 | S | |
| 200 | i-C3H7 | H | i-C3H7 | CH3 | H | OC(O) | 6-CH3 | S | |
| 201 | i-C3H7 | H | i-C3H7 | CH3 | H | OC(O) | 4,7-Cl2 | S | |

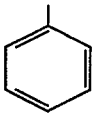

-continued

| | | | | | | | | |
|---|---|---|---|---|---|---|---|---|
| 202 | i-C₃H₇ | H | i-C₃H₇ | CH₃ | H | OC(O) | 5,7-Cl₂ | S | L |
| 203 | i-C₃H₇ | H | i-C₃H₇ | CH₃ | H | OC(O) | 3-OCH₃ | S | L |
| 204 | Ph | H | i-C₃H₇ | CH₃ | H | OC(O) | 5-F | S | L | 174–180 |
| 205 | Ph | H | i-C₃H₇ | CH₃ | H | OC(O) | 5-Cl | S | L | 194–198 |
| 206 | Ph | H | i-C₃H₇ | CH₃ | H | OC(O) | 5-Br | S | L | 158–163 |
| 207 | Ph | H | i-C₃H₇ | CH₃ | H | OC(O) | 5-CN | S | L |
| 208 | Ph | H | i-C₃H₇ | CH₃ | H | OC(O) | 5-CH₃ | S | L |
| 209 | Ph | H | i-C₃H₇ | CH₃ | H | OC(O) | 5-OCH₃ | S | L |
| 210 | Ph | H | i-C₃H₇ | CH₃ | H | OC(O) | 5-CF₃ | S | L |
| 211 | Ph | H | i-C₃H₇ | CH₃ | H | OC(O) | 4-CH₃ | S | L |

-continued

| No. | Ar | | | | | | | | | mp |
|---|---|---|---|---|---|---|---|---|---|---|
| 212 | Ph | H | i-C₃H₇ | CH₃ | H | OC(O) | 6-CH₃ | S | L | |
| 213 | Ph | H | i-C₃H₇ | CH₃ | H | OC(O) | 4,7-Cl₂ | S | L | |
| 214 | Ph | H | i-C₃H₇ | CH₃ | H | OC(O) | 5,7-Cl₂ | S | L | |
| 215 | Ph | H | i-C₃H₇ | CH₃ | H | OC(O) | 3-OCH₃ | S | L | |
| 216 | Ph | H | i-C₃H₇ | CH₃ | H | OC(O) | 3-Cl | S | L | |
| 217 | Ph | H | i-C₃H₇ | CH₃ | H | OC(O) | 4-Cl | S | L | |
| 218 | Ph | H | i-C₃H₇ | CH₃ | H | OC(O) | 7-Cl | S | L | |
| 219 | i-C₃H₇ | H | i-C₃H₇ | CH₃ | H | OC(O) | 3-Cl | S | L | |
| 220 | i-C₃H₇ | H | i-C₃H₇ | CH₃ | H | OC(O) | 4-Cl | S | L | |
| 221 | i-C₃H₇ | H | i-C₃H₇ | CH₃ | H | OC(O) | 7-Cl | S | L | |
| 222 | i-C₃H₇ | H | i-C₃H₇ | CN | H | OC(O) | H | O | L | |
| 223 | Ph | H | i-C₃H₇ | CN | H | OC(O) | H | O | L | 140–145 |
| 224 | i-C₃H₇ | H | i-C₃H₇ | CN | H | OC(O) | H | S | L | |

-continued

| | | | | | | | | | | |
|---|---|---|---|---|---|---|---|---|---|---|
| | 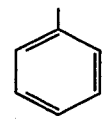 | H | i-C₃H₇ | CN | H | OC(O) | | S | L | |
| 225 | i-C₃H₇ | | | | | | | | | |
| 226 | t-C₄H₉ | H | i-C₃H₇ | C₂H₅ | H | OC(O) | 5-Cl | O | L | |
| 227 | t-C₄H₉ | H | i-C₃H₇ | CH₃ | H | OC(O) | H | NH | L | 69-70 |
| 228 | t-C₄H₉ | H | i-C₃H₇ | CH₃ | H | OC(O) | 5-Cl | NH | L | 115-120 |
| 229 | t-C₄H₉ | H | i-C₃H₇ | CH₃ | H | OC(O) | 5-CH₃ | NH | L | |
| 230 | t-C₄H₉ | H | i-C₃H₇ | CH₃ | H | OC(O) | 5-OCH₃ | NH | L | 50-56 |
| 231 | t-C₄H₉ | H | i-C₃H₇ | CH₃ | H | OC(O) | 5-NO₂ | NH | L | |
| 232 | t-C₄H₉ | H | i-C₃H₇ | CH₃ | H | OC(O) | 5-CN | NH | L | |
| 233 | t-C₄H₉ | H | i-C₃H₇ | CH₃ | H | OC(O) | H | NCH₃ | L | 161-166 |
| 234 | t-C₄H₉ | H | i-C₃H₇ | CH₃ | H | OC(O) | 5-Cl | NCH₃ | L | 175-178 |
| 235 | t-C₄H₉ | H | i-C₃H₇ | CH₃ | H | OC(O) | 5-CH₃ | NCH₃ | L | 152-155 |
| 236 | t-C₄H₉ | H | i-C₃H₇ | CH₃ | H | OC(O) | 5-OCH₃ | NCH₃ | L | |
| 237 | t-C₄H₉ | H | i-C₃H₇ | CH₃ | H | OC(O) | 5-NO₂ | NCH₃ | L | 107-110 |
| 238 | t-C₄H₉ | H | i-C₃H₇ | CH₃ | H | OC(O) | 5-CN | NCH₃ | L | 155-156 |
| 239 | t-C₄H₉ | H | i-C₃H₇ | CH₃ | H | OC(O) | 3-CH₃ | NH | L | |
| 240 | t-C₄H₉ | H | i-C₃H₇ | CH₃ | H | OC(O) | 3-CH₃ | O | L | |
| 241 | t-C₄H₉ | H | i-C₃H₇ | CH₃ | H | OC(O) | 6-OCH₃ | O | L | |
| 242 | t-C₄H₉ | H | i-C₃H₇ | CH₃ | H | OC(O) | 7-OCH₃ | NCH₃ | L | |
| 243 | t-C₄H₉ | H | i-C₃H₇ | CH₃ | H | OC(O) | 5-CF₃ | NCH₃ | L | |
| 244 | t-C₄H₉ | H | i-C₃H₇ | CH₃ | H | OC(O) | 3-Cl | NH | L | |
| 245 | t-C₄H₉ | H | i-C₃H₇ | CH₃ | H | OC(O) | 4-Cl | NH | L | |
| 246 | t-C₄H₉ | H | i-C₃H₇ | CH₃ | H | OC(O) | 6-Cl | NH | L | |
| 247 | t-C₄H₉ | H | i-C₃H₇ | CH₃ | H | OC(O) | 7-Cl | NH | L | |
| 248 | t-C₄H₉ | H | i-C₃H₇ | CH₃ | H | OC(O) | 4-CH₃ | NH | L | |
| 249 | t-C₄H₉ | H | i-C₃H₇ | CH₃ | H | OC(O) | 5-CH₃ | NH | L | |
| 250 | t-C₄H₉ | H | i-C₃H₇ | CH₃ | H | OC(O) | 6-CH₃ | NH | L | |
| 251 | t-C₄H₉ | H | i-C₃H₇ | CH₃ | H | OC(O) | 7-CH₃ | NH | L | |
| 252 | t-C₄H₉ | H | i-C₃H₇ | CH₃ | H | OC(O) | 4-OCH₃ | NH | L | |
| 253 | t-C₄H₉ | H | i-C₃H₇ | CH₃ | H | OC(O) | 6-OCH₃ | NH | L | |
| 254 | t-C₄H₉ | H | i-C₃H₇ | CH₃ | H | OC(O) | 7-OCH₃ | NH | L | |
| 255 | t-C₄H₉ | H | i-C₃H₇ | CH₃ | H | OC(O) | 4-CN | NH | L | |
| 256 | t-C₄H₉ | H | i-C₃H₇ | CH₃ | H | OC(O) | 6-CN | NH | L | |
| 257 | t-C₄H₉ | H | i-C₃H₇ | CH₃ | H | OC(O) | 7-CN | NH | L | |
| 258 | t-C₄H₉ | H | i-C₃H₇ | CH₃ | H | OC(O) | 4-NO₂ | NH | L | |
| 259 | t-C₄H₉ | H | i-C₃H₇ | CH₃ | H | OC(O) | 6-NO₂ | NH | L | |
| 260 | t-C₄H₉ | H | i-C₃H₇ | CH₃ | H | OC(O) | 7-NO₂ | NH | L | |
| 261 | t-C₄H₉ | H | i-C₃H₇ | CH₃ | H | OC(O) | 3-CH₃, 5-Cl | NH | L | |
| 262 | t-C₄H₉ | H | i-C₃H₇ | CH₃ | H | OC(O) | 3,5-(CH₃)₂ | NH | L | |
| 263 | t-C₄H₉ | H | i-C₃H₇ | CH₃ | H | OC(O) | 3,5-Cl₂ | NH | L | |
| 264 | t-C₄H₉ | H | i-C₃H₇ | CH₃ | H | OC(O) | 4,7-Cl₂ | NH | L | |
| 265 | t-C₄H₉ | H | i-C₃H₇ | CH₃ | H | OC(O) | 5,7-Cl₂ | NH | L | |
| 266 | t-C₄H₉ | H | i-C₃H₇ | CH₃ | H | OC(O) | 4,6-Cl₂ | NH | L | |
| 267 | t-C₄H₉ | H | i-C₃H₇ | CH₃ | H | OC(O) | H | NH | L | |
| 268 | i-C₃H₇ | H | i-C₃H₇ | CH₃ | H | OC(O) | 5-Cl | NH | L | |
| 269 | i-C₃H₇ | H | i-C₃H₇ | CH₃ | H | OC(O) | 5-CH₃ | NH | L | |
| 270 | i-C₃H₇ | H | i-C₃H₇ | CH₃ | H | OC(O) | 5-CH₃ | NH | L | |
| 271 | i-C₃H₇ | H | i-C₃H₇ | CH₃ | H | OC(O) | 5-OCH₃ | NH | L | |

| No. | Ar | | | | | | | | |
|---|---|---|---|---|---|---|---|---|---|
| 272 | i-C₃H₇ | H | i-C₃H₇ | CH₃ | H | OC(O) | 5-NO₂ | NH | L |
| 273 | i-C₃H₇ | H | i-C₃H₇ | CH₃ | H | OC(O) | 5-CN | NH | L |
| 274 | i-C₃H₇ | H | i-C₃H₇ | CH₃ | H | OC(O) | H | NCH₃ | L |
| 275 | Ph | H | i-C₃H₇ | CH₃ | H | OC(O) | 5-Cl | NCH₃ | L |
| 276 | Ph | H | i-C₃H₇ | CH₃ | H | OC(O) | 5-CH₃ | NCH₃ | L |
| 277 | Ph | H | i-C₃H₇ | CH₃ | H | OC(O) | 5-CH₃O | NCH₃ | L |
| 278 | Ph | H | i-C₃H₇ | CH₃ | H | OC(O) | 5-NO₂ | NCH₃ | L |
| 279 | Ph | H | i-C₃H₇ | CH₃ | H | OC(O) | 5-CN | NCH₃ | L |
| 280 | Ph | H | i-C₃H₇ | CH₃ | H | OC(O) | H | NCH₃ | L |
| 281 | C₂H₅ | H | i-C₃H₇ | CH₃ | H | OC(O) | H | NCH₃ | L |
| 282 | C₂H₅ | H | i-C₃H₇ | CH₃ | H | OC(O) | H | NH | L |
| 283 | t-C₄H₉ | H | i-C₃H₇ | CN | H | OC(O) | H | NH | L |
| 284 | t-C₄H₉ | H | i-C₃H₇ | CN | H | OC(O) | H | NCH₃ | L |
| 285 | i-C₃H₇ | H | i-C₃H₇ | CN | H | OC(O) | H | NH | L |
| 286 | i-C₃H₇ | H | i-C₃H₇ | CN | H | OC(O) | H | NCH₃ | L |
| 287 | Ph | H | i-C₃H₇ | CN | H | OC(O) | H | NH | L |

-continued

| No. | R1 | R2 | R3 | R4 | X | Y | Z | L | mp (°C) |
|---|---|---|---|---|---|---|---|---|---|
| 288 | phenyl | H | i-C₃H₇ | CN | H | OC(O) | H | NCH₃ | L |  |
| 289 | t-C₄H₉ | H | i-C₃H₇ | CH₃ | H | OC(O) | H | NC(O)CH₃ | L |  |
| 290 | i-C₃H₇ | H | i-C₃H₇ | CH₃ | H | OC(O) | H | NC(O)CH₃ | L |  |
| 291 | t-C₄H₉ | H | i-C₃H₇ | CH₃ | H | OC(O) | H | N=C(phenyl) | L |  |
| 292 | i-C₃H₇ | H | i-C₃H₇ | CH₃ | H | OC(O) | H | N=C(phenyl) | L |  |
| 293 | t-C₄H₉ | H | i-C₃H₇ | CH₃ | H | OC(O) | H | N=C(phenyl) | L |  |
| 294 | t-C₄H₉ | H | i-C₃H₇ | CH₃ | H | OC(O) | 5-Cl | NC(O)CH₃ | L |  |
| 295 | phenyl | H | i-C₃H₇ | CH₃ | H | OC(O) | 5-Cl | O | L |  |
| 296 | i-C₃H₇ | H | i-C₃H₇ | CH₃ | H | OC(O) | 5-Cl | O | L | 211–216 |
| 297 | 4-CH₃O-C₆H₄-CH₂ | H | i-C₃H₇ | CH₃ | H | OC(O) | 5-Cl | O | L |  |
| 298 | cyclohex-1-enyl | H | i-C₃H₇ | CH₃ | H | OC(O) | 5-Cl | O | L |  |
| 299 | cyclohex-2-enyl | H | i-C₃H₇ | CH₃ | H | OC(O) | 5-Cl | O | L |  |

| No. | R | | | | | | | | mp |
|---|---|---|---|---|---|---|---|---|---|
| 300 | (1-methylcyclopentenyl) | H | i-C₃H₇ | CH₃ | H | OC(O) | 5-Cl | O | L | |
| 301 | (4-methylcyclopentenyl) | H | i-C₃H₇ | CH₃ | H | OC(O) | 5-Cl | O | L | |
| 302 | i-C₃H₇ | H | i-C₃H₇ | CH₃ | H | OC(O) | H | O | L | 221-223 |
| 303 | (methylcyclopentyl) | H | i-C₃H₇ | CH₃ | H | OC(O) | 5-Cl | O | L | |
| 304 | i-C₃H₇ | H | i-C₃H₇ | H | H | OC(O) | 5-Cl | O | L | 177-180 |
| 305 | t-C₄H₉ | H | i-C₃H₇ | H | H | OC(O) | 5-NO₂ | O | L | 110-112 |
| 306 | C₂H₅ | H | i-C₃H₇ | H | H | OC(O) | 5-NO₂ | O | L | |
| 307 | CH₂=C(CH₃)— | H | i-C₃H₇ | H | H | OC(O) | 5-NO₂ | O | L | |
| 308 | i-C₃H₇ | H | i-C₃H₇ | CH₃ | C(O)CH₃ | OC(O) | H | O | L | |
| 309 | t-C₄H₉ | H | i-C₃H₇ | CH₃ | (benzoyl) | OC(O) | 5-CN | O | L | |
| 310 | CH₃(CH₂)₂—CH(CH₃)— | H | i-C₃H₇ | CH₃ | C(O)OCH₃ | OC(O) | 5-NO₂ | O | L | 200-203 |
| 311 | | H | i-C₃H₇ | CH₃ | C(O)OC₂H₅ | OC(O) | 5-Cl | O | L | 152-155 |
| 312 | | H | i-C₃H₇ | CH₃ | H | OC(O) | 5-NO₂ | O | L | |
| 313 | | H | i-C₃H₇ | CH₃ | H | OC(O) | 5-F | O | L | |
| 314 | CH₃(CH₂)₂—CH(CH₃)— | H | i-C₃H₇ | CH₃ | H | OC(O) | 5-Cl | O | L | 116-121 |
| 315 | CH₃(CH₂)₂—CH(CH₃)— | H | i-C₃H₇ | CH₃ | H | OC(O) | 5-Cl | O | L | 114-119 |
| 316 | CH₂=C(CH₃)— | H | i-C₃H₇ | CH₃ | H | OC(O) | 5-NO₂ | O | L | 159-162 |
| 317 | i-C₃H₇ | H | i-C₃H₇ | C₂H₅ | H | OC(O) | 5-Cl | O | L | 169-173 |
| 318 | (phenyl) | H | i-C₃H₇ | CH₃ | H | SC(S) | 5-Cl | O | L | 74-79 |

-continued

| No. | | | | | | | | mp |
|---|---|---|---|---|---|---|---|---|
| 319 | CH₂=C(CH₃)— | H | i-C₃H₇ | CH₃ | H | OC(O) | 5-CN | O | L | 187–189 |
| 320 | CH(CH₃)(C₂H₅) (stereo) | H | i-C₃H₇ | CH₃ | H | OC(O) | 5-Cl | O | L | 155–161 |
| 321 | CH(CH₃)(C₂H₅) (stereo) | H | i-C₃H₇ | CH₃ | H | OC(O) | 5-Cl | O | L | 170–175 |
| 322 | C₂H₅ | H | i-C₃H₇ | CH₃ | H | OC(O) | H | O | L | 156–157 |
| 323 | C₂H₅ | H | i-C₃H₇ | CH₃ | H | OC(O) | H | O | L | 170–175 |
| 324 | cyclohexyl | H | i-C₃H₇ | CH₃ | H | OC(O) | H | O | L | 169–174 |
| 325 | cyclopentyl | H | i-C₃H₇ | CH₃ | H | OC(O) | H | O | L | 114–117 |
| 326 | s-C₄H₉ | H | i-C₃H₇ | CH₃ | H | OC(O) | H | O | L | 146–148 |
| 327 | CH₂=C(CH₃)— / i-C₃H₇ | H | i-C₃H₇ | CH₃ | H | OC(O) | 5-F | O | L | 179–182 |
| 328 | phenyl | H | i-C₃H₇ | H | H | OC(O) | 5-Cl | O | L | 177–179 |
| 329 | NCC(CH₃)₂ | H | i-C₃H₇ | CH₃ | H | OC(O) | 5-Cl | O | L | 122–127 |
| 330 | t-C₄H₉ | H | i-C₃H₇ | C₃H₇ | H | OC(O) | 5-Cl | O | L | 95–99 |
| 331 | i-C₃H₇ | H | i-C₃H₇ | C₃H₇ | H | OC(O) | 5-Cl | O | L | 155–160 |
| 332 | CH(CH₃)(phenyl) | H | i-C₃H₇ | CH₃ | H | OC(O) | 5-Cl | O | L | 154–157 |
| 333 | i-C₃H₇ | H | i-C₃H₇ | CH₃ | H | OC(O) | 5-C₅H₁₁ | O | L | 98–100 |
| 334 | t-C₄H₉ | H | i-C₃H₇ | CH₃ | H | OC(O) | 5-C₉H₁₉ | O | L | 55–58 |
| 335 | CH₃OCH₂—CH(CH₃)— | H | i-C₃H₇ | CH₃ | H | OC(O) | 5-Cl | O | L | 125–128 |

-continued

| No. | Ar | | | | | | | | | mp/nD |
|---|---|---|---|---|---|---|---|---|---|---|
| 336 | (3-methyltetrahydrofuran) | H | i-C₃H₇ | CH₃ | H | OC(O) | 5-Cl | O | L | 192–195 |
| 337 | (3-methyltetrahydrofuran) | H | i-C₃H₇ | CH₃ | H | OC(O) | 5-Cl | O | L | 195–197 |
| 338 | i-C₃H₇ | H | s-C₄H₉ | CH₃ | H | OC(O) | 5-Cl | O | L | 159–163 |
| 339 | i-C₃H₇ | H | s-C₄H₉ | CH₃ | H | OC(O) | 5-Cl | O | L | 170–176 |
| 340 | phenyl | H | C₂H₅ | CH₃ | H | OC(O) | 5-Cl | O | L | 151–154 |
| 341 | i-C₃H₇-phenyl | H | C₂H₅ | CH₃ | H | OC(O) | 5-Cl | O | L | 158–160 |
| 342 | i-C₃H₇ | H | i-C₃H₇ | CH₃ | CH₃ | OC(O) | 5-Cl | O | L | 1,5280 |
| 343 | i-C₃H₇ | H | i-C₃H₇ | CH₃ | OCH₃ | OC(O) | 5-Cl | O | L | 61–64 |
| 344 | t-C₄H₉ | H | i-C₃H₇ | CH₃ | H | OC(O) | 6-Cl | S | L | 184–186 |
| 345 | i-C₃H₇ | H | i-C₃H₇ | H | H | OC(O) | H | S | L | |
| 346 | benzyl (CH₂-phenyl) | H | i-C₃H₇ | CH₃ | H | OC(O) | H | S | L | 160–161 |
| 347 | t-C₄H₉ | H | i-C₃H₇ | H | H | OC(O) | 3-CH₃ | S | L | 143–144 |
| 348 | i-C₃H₇ | H | i-C₃H₇ | H | H | OC(O) | 3-CH₃ | S | L | 188–189 |
| 349 | s-C₄H₉ | H | i-C₃H₇ | H | H | OC(O) | 3-CH₃ | S | L | 161–162 |
| 350 | benzyl (CH₂-phenyl) | H | i-C₃H₇ | H | H | OC(O) | 3-CH₃ | S | L | 196–197 |
| 351 | t-C₄H₉ | H | i-C₃H₇ | CH₃ | H | OC(O) | 5-F | NH | L | 79–81 |
| 352 | i-C₃H₇ | H | i-C₃H₇ | CH₃ | H | OC(O) | 5-F | NH | L | 152–154 |

| No. | Ar | R1 | R2 | R3 | X | Y | L | mp |
|---|---|---|---|---|---|---|---|---|
| 353 | phenyl | H | i-C3H7 | CH3 | H | OC(O) 5-F | NH | L | 162–166 |
| 354 | cyclopentyl | H | i-C3H7 | H | H | OC(O) 3-CH3 | S | L | 195–198 |
| 355 | phenyl | H | i-C3H7 | H | H | OC(O) 3-CH3 | S | L | 204–207 |
| 356 | phenyl | t-C4H9 | i-C3H7 | CH3 | H | OC(O) 5-F | NCH3 | L | 73–76 |
| 357 | phenyl | i-C3H7 | i-C3H7 | CH3 | H | OC(O) 5-F | NCH3 | L | 163–166 |
| 358 | phenyl | t-C4H9 | i-C3H7 | CH3 | H | OC(O) 6-OCH3 | S | L | 146–150 |
| 359 | phenyl | i-C3H7 | i-C3H7 | CH3 | H | OC(O) 6-Cl | S | L | 171–176 |
| 360 | phenyl | i-C3H7 | i-C3H7 | CH3 | H | OC(O) 6-OCH3 | S | L | 184–185 |
| 361 | phenyl | H | i-C3H7 | CH3 | H | OC(O) 5-F | NCH3 | L | 153–156 |
| 362 | phenyl | t-C4H9 | i-C3H7 | CH3 | H | OC(O) H | NH | L | 70–72 |
| 363 | phenyl | t-C4H9 | i-C3H7 | CH3 | H | OC(O) H | NCH3 | L | 211–213 |
| 364 | phenyl | t-C4H9 | i-C3H7 | CH3 | H | OC(O) 5-Cl | NH | L | 192–196 |
| 365 | phenyl | s-C4H9 | i-C3H7 | CH3 | H | OC(O) 5-OCH3 | NH | L | 75–79 |
| 366 | phenyl | s-C4H9 | i-C3H7 | CH3 | H | OC(O) 5-Cl | S | L | 145–149 |
| 367 | cyclopentyl | H | i-C3H7 | CH3 | H | OC(O) 5-Cl | S | L | 179–184 |
| 368 | i-C3H7 | H | i-C3H7 | CH3 | H | OC(O) 5-Cl | NCH3 | L | 121–124 |
| 369 | benzyl (CH2-phenyl) | H | i-C3H7 | CH3 | H | OC(O) 5-Cl | NCH3 | L | 202–204 |
| 370 | i-C3H7 | H | i-C3H7 | CH3 | H | OC(O) 6-F | S | L | 160–170 |
| 371 | t-C4H9 | H | i-C3H7 | CH3 | H | OC(O) 5-CN | NH | L | |
| 372 | i-C3H7 | H | i-C3H7 | CH3 | H | OC(O) 5-CN | NH | L | |
| 373 | t-C4H9 | H | i-C3H7 | CH3 | OCH3 | OC(O) 5-CN | NH | L | |

-continued
| | | | | | | | |
|---|---|---|---|---|---|---|---|
| 374 | H | i-C₃H₇ | CH₃ | OCH₃ | OC(O) | 5-CN | NH | 236-239 |
| 375 | H | i-C₃H₇ | CH₃ | H | OC(O) | 5-NO₂ | O | 163-164 |
| 376 | h | i-C₃H₇ | CH₃ | H | OC(O) | H | S | 117-119 |
| 377 | H | t-C₄H₉ | CH₃ | H | OC(O) | 5-Cl | O | 128-130 |
| 378 | H | t-C₄H₉ | CH₃ | H | OC(O) | 5-Cl | O | 164-164 |
| 379 | H | t-C₄H₉ | CH₃ | H | OC(O) | 5-Cl | O | 89-94 |
| 380 | H | t-C₄H₉ | CH₃ | H | OC(O) | 5-F | O | 120-124 |
| 381 | H | t-C₄H₉ | CH₃ | H | OC(O) | 5-Br | O | 135-139 |
| 382 | H | t-C₄H₉ | CH₃ | H | OC(O) | 5-NO₂ | O | 68-73 |
| 383 | H | t-C₄H₉ | CH₃ | H | OC(O) | 5-CF₃ | O | |
| 384 | H | i-C₃H₇ | CH₃ | H | OC(O) | 5-Cl | O | 188-190 |
| 385 | H | i-C₃H₇ | CH₃ | H | OC(O) | 5-Cl | O | 170-175 |
| 386 | H | i-C₃H₇ | CH₃ | H | OC(O) | 5-Cl | O | 185-189 |
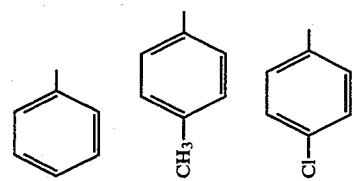

TABLE 2

$$R^1-W-NH-\underset{\underset{R^3}{|}}{\overset{\overset{R^2}{|}}{C}}-\overset{\overset{O}{\|}}{C}-\underset{\underset{R^5}{|}}{N}-\overset{\overset{R^4}{|}}{CH}\underset{2}{\overset{3}{\diagdown}}\underset{A_1}{\diagup}\underset{7}{\overset{4}{\diagdown}}\underset{6}{\overset{5\,X_n}{\diagdown}}$$

| Compound No. | R¹ | R² | R³ | R⁴ | R⁵ | W | Xn | A | Amino Acid Isomer | Melting Point (°C.) or Refractive Index ($n_D^{20}$) |
|---|---|---|---|---|---|---|---|---|---|---|
| 387 | t-C₄H₉ | H | i-C₃H₇ | CH₃ | H | OC(O) | H | O | L | 144–148 |
| 388 | i-C₃H₇ | H | i-C₃H₇ | CH₃ | H | OC(O) | H | O | L | 159–164 |
| 389 | t-C₄H₉ | H | i-C₃H₇ | CH₃ | H | OC(O) | 5-CH₃ | O | L | not determined |
| 390 | t-C₄H₉ | H | i-C₃H₇ | CH₃ | H | OC(O) | H | S | L | |
| 391 | i-C₃H₇ | H | i-C₃H₇ | CH₃ | H | OC(O) | H | S | L | |
| 392 | C₆H₅ | H | i-C₃H₇ | CH₃ | H | OC(O) | H | S | L | |
| 393 | t-C₄H₉ | H | i-C₃H₇ | CH₃ | H | OC(O) | 5-Cl | O | L | 58–60 |
| 394 | t-C₄H₉ | H | i-C₃H₇ | CH₃ | H | OC(O) | 5-NO₂ | O | L | |
| 395 | i-C₃H₇ | H | i-C₃H₇ | CH₃ | H | OC(O) | 5-Cl | O | L | 132–135 |
| 396 | i-C₃H₇ | H | i-C₃H₇ | CH₃ | H | OC(O) | 5-NO₂ | O | L | |
| 397 | C₆H₅ | H | i-C₃H₇ | CH₃ | H | OC(O) | 5-CN | O | L | not determined |
| 398 | t-C₄H₉ | H | i-C₃H₇ | CH₃ | H | OC(O) | 5-CN | O | L | not determined |
| 399 | C₆H₅ | H | i-C₃H₇ | CH₃ | H | OC(O) | 5-Cl | O | L | 134–139 |
| 400 | C₆H₅CH₂— | H | i-C₃H₇ | CH₃ | H | OC(O) | 5-F | O | L | 126–130 |
| 401 | i-C₃H₇ | H | i-C₃H₇ | CH₃ | H | OC(O) | 5-F | O | L | 160–163 |
| 402 | C₆H₅ | H | i-C₃H₇ | CH₃ | H | OC(O) | 5-F | O | L | not determined |
| 403 | t-C₄H₉ | H | i-C₃H₇ | CH₃ | H | OC(O) | 5-F | O | L | <30 |
| 404 | t-C₄H₉ | H | i-C₃H₇ | CH₃ | H | OC(O) | H | NCH₃ | L | 99–103 |

TABLE 3

$$R^1-W-NH-\underset{\underset{R^3}{|}}{\overset{\overset{R^2}{|}}{C}}-\overset{\overset{O}{\|}}{C}-\underset{\underset{R^5}{|}}{N}-\overset{\overset{R^4}{|}}{CH}\underset{2}{\overset{3}{\diagdown}}\underset{A_1}{\diagup}\underset{7}{\overset{4}{\diagdown}}\underset{6}{\overset{5\,X_n}{\diagdown}}$$

| Compound No. | R¹ | R² | R³ | R⁴ | R⁵ | W | Xn | A | Amino Acid Isomer | Melting Point (°C.) or Refractive Index ($n_D^{20}$) |
|---|---|---|---|---|---|---|---|---|---|---|
| 405 | t-C₄H₉ | H | i-C₃H₇ | CH₃ | H | OC(O) | H | NH | L | 83–86 |
| 406 | t-C₄H₉ | H | i-C₃H₇ | CH₃ | H | OC(O) | H | NH | L | 89–94 |
| 407 | t-C₄H₉ | H | i-C₃H₇ | CH₃ | H | OC(O) | H | N—CH₃ | L | 128–130 |
| 408 | t-C₄H₉ | H | i-C₃H₇ | CH₃ | H | OC(O) | H | O | L | |
| 409 | t-C₄H₉ | H | i-C₃H₇ | CH₃ | H | OC(O) | H | S | L | |

TABLE 4

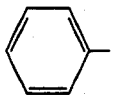

| Compound No. | R¹ | R² | R³ | R⁴ | R⁶ | Xn | A | Amino Acid Isomer | Melting Point (°C.) or Refractive Index ($n_D^{20}$) |
|---|---|---|---|---|---|---|---|---|---|
| 410 | t-C₄H₉ | H | i-C₃H₇ | CH₃ | CH₃ | H | O | L | |
| 411 | i-C₃H₇ | H | i-C₃H₇ | CH₃ | CH₃ | H | O | L | |
| 412 | C₆H₅ | H | i-C₃H₇ | CH₃ | CH₃ | H | O | L | |
| 413 | t-C₄H₉ | H | i-C₃H₇ | CH₃ | CH₃ | 5-Cl | O | L | 44–46 |
| 414 | i-C₃H₇ | H | i-C₃H₇ | CH₃ | CH₃ | 5-Cl | O | L | 68–69 |
| 415 | C₆H₅ | H | i-C₃H₇ | CH₃ | CH₃ | 5-Cl | O | L | |
| 416 | i-C₃H₇ | H | i-C₃H₇ | CH₃ | CH₃ | 5-NO₂ | O | L | |
| 417 | t-C₄H₉ | H | i-C₃H₇ | CH₃ | CH₃ | H | S | L | 162–165 |
| 418 | i-C₃H₇ | H | i-C₃H₇ | CH₃ | CH₃ | H | S | L | |
| 419 | t-C₄H₉ | CH₃ | i-C₃H₇ | CH₃ | CH₃ | H | O | DL | |
| 420 | t-C₄H₉ | H | i-C₃H₇ | CH₃ | C₂H₅ | H | O | L | |
| 421 | t-C₄H₉ | H | i-C₃H₇ | CH₃ | i-C₃H₇ | H | O | L | |
| 422 | sec-C₄H₉ | H | i-C₃H₇ | CH₃ | CH₃ | 5-Cl | O | L | |

TABLE 5

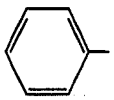

| Compound No. | R¹ | R² | R³ | R⁴ | R⁵ | W | Xn | A | Amino Acid Isomer | Melting Point (°C.) or Refractive Index ($n_D^{20}$) |
|---|---|---|---|---|---|---|---|---|---|---|
| 423 | t-C₄H₉ | H | i-C₃H₇ | CH₃ | H | OC(O) | H | N | L | 178–182 |
| 424 | t-C₄H₉ | H | i-C₃H₇ | CH₃ | H | OC(O) | H | N | L | 124–127 |
| 425 | i-C₃H₇ | H | i-C₃H₇ | CH₃ | H | OC(O) | H | N | L | 186–190 |
| 426 | C₆H₅ | H | i-C₃H₇ | CH₃ | H | OC(O) | H | N | L | 151–154 |

TABLE 6

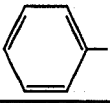

| Compound No. | R¹ | R² | R³ | R⁴ | R⁵ | W | Xn | A | Amino Acid Isomer | Melting Point (°C.) or Refractive Index ($n_D^{20}$) |
|---|---|---|---|---|---|---|---|---|---|---|
| 427 | t-C₄H₉ | H | i-C₃H₇ | CH₃ | H | OC(O) | H | NH | L | not determined |
| 428 | t-C₄H₉ | H | i-C₃H₇ | CH₃ | H | OC(O) | H | NCH₃ | L | 160–162 |
| 429 | i-C₃H₇ | H | i-C₃H₇ | CH₃ | H | OC(O) | H | NH | L | |

TABLE 6-continued $$R^1-W-NH-\underset{\underset{R^3}{|}}{\overset{\overset{R^2}{|}}{C}}-\overset{\overset{O}{\|}}{C}-\underset{\underset{R^5}{|}}{N}-\overset{\overset{R^4}{|}}{CH}-A\text{-naphthyl-}X_n$$

| Compound No. | $R^1$ | $R^2$ | $R^3$ | $R^4$ | $R^5$ | W | $X_n$ | A | Amino Acid Isomer | Melting Point (°C.) or Refractive Index ($n_D^{20}$) |
|---|---|---|---|---|---|---|---|---|---|---|
| 430 | 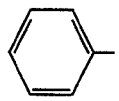 | H | i-$C_3H_7$ | $CH_3$ | H | OC(O) | H | NH | L | |

TABLE 7

$$R^1-W-NH-\underset{\underset{R^3}{|}}{\overset{\overset{R^2}{|}}{C}}-\overset{\overset{O}{\|}}{C}-\underset{\underset{R^5}{|}}{N}-\overset{\overset{R^4}{|}}{CH}-A\text{=naphthyl-}X_n$$

| Compound No. | $R^1$ | $R^2$ | $R^3$ | $R^4$ | $R^5$ | W | $X_n$ | A | Amino Acid Isomer | Melting Point (°C.) or Refractive Index ($n_D^{20}$) |
|---|---|---|---|---|---|---|---|---|---|---|
| 431 | t-$C_4H_9$ | H | i-$C_3H_7$ | $CH_3$ | H | OC(O) | H | O | L | |
| 432 | i-$C_3H_7$ | H | i-$C_3H_7$ | $CH_3$ | H | OC(O) | H | O | L | not determined |
| 433 | 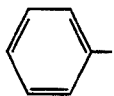 | H | i-$C_3H_7$ | $CH_3$ | H | OC(O) | H | O | L | |

The compounds represented by formula [I] according to the present invention can be prepared in the following manner.

Preparation Process A

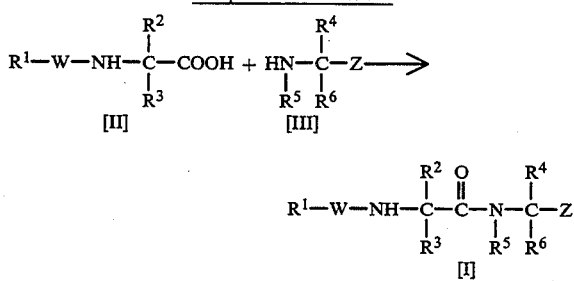

wherein $R^1$, $R^2$, $R^3$, $R^4$, $R^5$, $R^6$, W and Z, are the same as described above.

The compounds represented by formula [I] according to the present invention can be prepared by reacting an amino acid derivative represented by formula [II] or the amino acid derivative wherein the carboxyl group is activated, with an amine represented by formula [III] in the presence of a base and/or a catalyst if necessary.

In the present reaction, as the amino acid derivative represented by formula [II] with an activated carboxyl group there can be mentioned, for example, an acid halide such as an acid chloride, an acid anhydride derived from the two molecules of the amino acid derivatives represented by formula [II], a mixed acid anhydride derived from the amino acid derivative represented by formula [II] and other acid or an O-alkyl carbonic acid, and an activated ester such as p-nitrophenyl ester, 2-tetrahydropyranyl ester, and 2-pyridyl ester and the like. These compounds can be synthesized according to conventional methods [for example, see Methoden der Organischen Chemie, Vol. 15, No. 2, from page 2; Georg Thieme Verlag Stuttgart: 1974; Chemische Berichte, Vol. 38, page 605 (1905); Journal of the American Chemical Society, Vol. 74. page 676 (1952); and Journal of the American Chemical Society, Vol. 86, page 1839 (1964)].

In addition, it is also possible to perform the present reaction using a condensing agent such as N, N'-dicyclohexylcarbodiimide, carbonyldiimidazole or the like.

The present reaction can be performed in a conventional solvent: this solvent can be any solvent that does not hinder the reaction, for example, hydrocarbons such as pentane, hexane, heptane, cyclohexane, petroleum ether, ligroin, benzene, toluene, xylene and the like, halogenated hydrocarbons such as dichloromethane, dichloroethane, chloroform, carbon tetrachloride, chlorobenzene, dichlorobenzene and the like, ethers such as diethyl ether, diisopropyl ether, ethylene glycol dimethyl ether, tetrahydrofuran, dioxane and the like, ketones such as acetone, methyl ethyl ketone, methyl isopropyl ketone, methyl isobutyl ketone and the like, esters such as methyl acetate, ethyl acetate and the like, nitriles such as acetonitrile, propionitrile, benzonitrile and the like, aprotic solvents such as dimethylsulfoxide, dimethylformamide, sulfolane and the like, and mixed solvents combining solvents selected from the aforementioned.

The base can be any type of base generally used in this type of reaction. For example, there can be mentioned hydroxides of alkaline metals such as sodium hydroxide, potassium hydroxide and the like, hydroxides of alkaline earth metals such as calcium hydroxide and the like, carbonates of alkaline metals such as potassium carbonate and the like, organic bases such as triethylamine, trimethylamine, dimethylaniline, pyridine, N-methylpiperidine, 1,5-diazabicyclo[4.3.0]non-5-ene (DBN), 1,8-diazadicyclo[5.4.0]undec-7-ene (DBU), and the like, and preferably tertiary amines such as triethylamine, pyridine, N-methylpiperidine and the like.

As the catalyst there can be mentioned 4-dimethylaminopyridine, 1hydroxybenzotriazole, dimethylformamide and the like. The present reaction is carried out at a temperature of −75° C. to 100° C., preferably −60° C. to 40%. The reaction time is preferably 1 to 20 hours.

Furthermore, compounds represented by formula [II] as the starting material are known and can generally be synthesized by conventional methods [for example, see Methoden der Organischen Chemie, Vol. 15, No. 2, from page 2; Georg Thieme Verlag Stuttgart: 1974; Chemistry of the Amino Acids, vol. 2, page 891; John Wiley & Sons, N.Y.( 1964); and Journal of the American Chemical Society, Vol. 79, page 4686 (1957)]. Various manufacturing methods for compounds [III] can also be considered such as those methods stated in Japanese patent application, First Publication No. Sho 63-146876 and Synthesis, page 24, 1978). The majority of compounds [III] represent novel compounds.

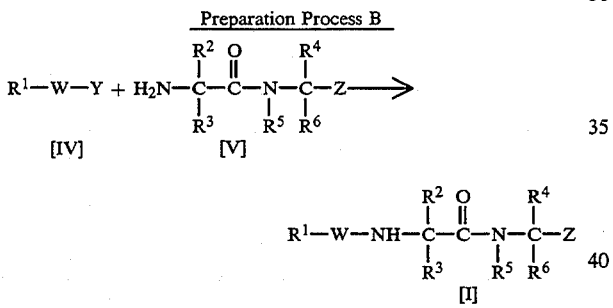

wherein $R^1$, $R^2$, $R^3$, $R^4$, $R^5$, $R^6$, W, and Z represent the same meanings as stated above, and Y represents a halogen atom, an $R^1OC(O)O-$ group or a $R^1C(O)O-$ group.

Compounds represented by formula [I] of the present invention can be manufactured by means of reacting the compound represented by formula [IV] with an amine represented by formula [V], a salt of the amine derivative with an inorganic acid such as hydrochloride and the like, or a salt of the amine derivative with an organic acid such as tosylate and the like, in the presence of a base when required.

The present reaction can be performed in a conventional solvent: this solvent can be any solvent that does not hinder the reaction, for example, hydrocarbons such as pentane, hexane, heptane, cyclohexane, petroleum ether, ligroin, benzene, toluene, xylene and the like, halogenated hydrocarbons such as dichloromethane, dichloroethane, chloroform, carbon tetrachloride, chlorobenzene, dichlorobenzene and the like, ethers such as diethyl ether, diisopropyl ether, ethylene glycol dimethyl ether, tetrahydrofuran, dioxane and the like, ketones such as acetone, methyl ethyl ketone, methyl isopropyl ketone, methyl isobutyl ketone and the like, esters such as methyl acetate, ethyl acetate and the like, nitriles such as acetonitrile, propionitrile, benzonitrile and the like, aprotic solvents such as dimethylsulfoxide, dimethylformamide, sulfolane and the like, water, and mixed solvents combining solvents selected from the aforementioned.

The base can be any type of base generally used in this type of reaction. For example, there can be mentioned hydroxides of alkaline metals such as sodium hydroxide, potassium hydroxide and the like, hydroxides of alkaline earth metals such as calcium hydroxide and the like, carbonates of alkaline metals such as potassium carbonate and the like, organic bases such as triethylamine, trimethylamine, dimethylaniline, N-methylmorpholine, pyridine, N-methylpiperidine, 1,5-diazadicyclo [4.3.0]non-5-ene (DBN), 1,8-diazadicyclo [5.4.0]undec-7-ene (DBU), and the like, and preferably tertiary amines such as triethylamine, pyridine, N-methylpiperidine and the like. The present reaction is carried out at a temperature of −20° C. to 100° C., preferably 0° C. to 40° C. The reaction time is preferably 30 minutes to 20 hours.

Compounds represented by formula [V] as the starting material represent novel compounds, and can be manufactured, for example, by means of treating carbamates of compounds [I] synthesized by the procedure of preparation process A using a conventional process for removing the amino protecting group of the amino acid such as catalytic reduction, or by treating with acids such as liquid hydrofluoric acid, sulfonic acids, hydrochloric acid, hydrobromic acid, formic acid and the like.

In the following, synthesis examples of condensed heterocyclic derivatives, which are novel intermediates of the compounds of the present invention represented by formulae [III] and [V], are provided as reference examples.

REFERENCE EXAMPLE 1

Synthesis of 1-[2-(5-nitrobenzofuranyl)]ethylamine (Intermediate Compound No. 1)

37 g of ammonium acetate and 2.1 g of sodium cyanoborohydride were added to a solution containing 10 g of 2-(5-nitrobenzofuranyl) methyl ketone dissolved in 500 ml of methanol, and the resultant mixture was stirred for 30 hours at room temperature. The reaction mixture was then concentrated under reduced pressure, and acidified with concentrated hydrochloric acid. 300 ml of ethyl ether and 200 ml of water were then added thereto. Subsequently, the resultant water layer was made basic with a 5% aqueous solution of sodium hydroxide, the solution was extracted with 300 ml of ethyl ether, and then washed with water. The organic layer was then dried over anhydrous sodium sulfate, and the ether was removed under reduced pressure to yield 4.0 g of light brown granular crystals as the desired product (melting point: 53°–59° C.).

REFERENCE EXAMPLE 2

Synthesis of 1-(6-chloro-2-benzo[b]thienyl)ethylamine (Intermediate Compound No. 2)

2.2 g of O-methylhydroxylamine hydrochloride and 1.3 g of potassium acetate were added to a solution containing 2.8 g of 2-acethyl-6-chlorobenzo[b]thiophene dissolved in 50 ml of methanol, and the resultant mixture was agitated under reflux for 1 hour. The undissolved material was then filtered off, and the methanol was removed. Subsequently, the residue was extracted with ethyl acetate, washed sequentially with 5% hydrochloric acid, a 5% aqueous solution of sodium bicarbonate, and water, and dried over anhydrous magnesium sulfate, and then concentrated.

Subsequently, 2.7 g of the crude 6-chloro-2-(1-methoxyiminoethyl)benzo[b]thiophene obtained was dissolved in 10 ml of dimethoxyethane, and the resultant solution was added dropwise at room temperature to a suspension of 0.85 g of sodium borohydride in 20 ml of dimethoxyethane. After agitating for 5 minutes at the same temperature, a solution containing 4.26 g of a boron trifluoride.diethyl ether complex in 5 ml of dimethoxyethane was then added dropwise at room temperature. After stirring for 30 minutes at the same temperature, the mixture was stirred for an additional 2 hours under reflux. The mixture was then allowed to cool to room temperature, after which 10% hydrochloric acid was added, adjusting the mixture to a pH of 3-4. The dimethoxyethane layer was concentrated and combined with the water layer, and the pH was raised to 7-8 using sodium carbonate. Extraction was then performed using dichloromethane, and the dichloromethane layer was then washed with water, dried over anhydrous magnesium sulfate, filtered through FLORISIL ®, and concentrated to yield 0.35 g of the desired product, a transparent viscous fluid (refractive index $n_D^{20}=1.5973$).

Specific examples of intermediate compound represented by formula [III] obtained through the operations of Reference Examples 1 and 2 are shown in Table 8.

REFERENCE EXAMPLE 3

Synthesis of
1-[2-(5-cyano-2,3-dihydrobenzofuranyl)]ethylamine
(Intermediate Compound No. 21)

4.0 g of ammonium acetate and 0.24 g of sodium cyanoborohydride were added to a solution containing 1.0 g of 2-(5-cyano-2,3-dihydrobenzofuranyl) methyl ketone (prepared according to the method stated in Org. Prep. Proced. Int. 4,265 (1972)) in 50 ml of methanol, and the resultant mixture was stirred for 30 hours at room temperature. The reaction mixture was then concentrated under reduced pressure, acidified with concentrated hydrochloric acid. 100 ml of ethyl ether and 50 ml of water were then added thereto. Subsequently, the resultant water layer was made basic with an aqueous solution of sodium hydroxide and extracted with 200 ml of ether. The organic layer was washed with water and dried over anhydrous magnesium sulfate. The ether was then removed under reduced pressure to yield 0.6 g of the desired product, a light-yellow oily substance (refractive index $n_D^{20}=1.5719$).

Specific examples of intermediate compound represented by formula [III] obtained through the operation of Reference Example 3 are shown in Table 9.

REFERENCE EXAMPLE 4

Synthesis of
1-[2-(5-chlorobenzofuranyl)ethyl-N-methylamine
(Intermediate Compound No. 25)

1.4 g of anhydrous methylamine hydrochloride was added to a 10 ml solution of 20% methylamine in methanol while agitating, following which 0.8 g of sodium cyanoborohydride was added in small portions. To the resultant solution, 2.8 g of 2-(5-chlorobenzofuranyl-)ethyl ketone was added and the mixture was stirred for 20 hours at room temperature. The reaction mixture was then acidified with 10% hydrochloric acid, and the methanol was removed under reduced pressure. The remaining aqueous solution was then washed with chloroform and made basic with an aqueous solution of sodium hydroxide. The solution was then extracted with 200 ml of chloroform, washed with water, and dried over anhydrous magnesium sulfate. The chloroform was subsequently removed under reduced pressure to yield 1.9 g of the desired product, a light-yellow oily substance (refractive index $n_D^{20}=1.5681$).

REFERENCE EXAMPLE 5

Synthesis of
$N^1$-[1-(5-nitro-2-benzofuranyl)ethyl]-L-valinamide
hydrochloride (Intermediate Compound No. 26)

5.0 g of $N^2$-tert-butoxycarbonyl-$N^1$-[1-(5-nitro-2-benzofuranyl)ethyl]-L-valinamide was dissolved in 100 ml of tetrahydrofuran, and placed in a flow of hydrogen chloride gas for 1 hour at room temperature. The reaction mixture was then concentrated under reduced pressure, and the residual crude crystals obtained were washed with acetone to yield 3.6 g of the desired product (melting point: 211°-216° C.).

REFERENCE EXAMPLE 6

Synthesis of
$N^1$-[1-(2-benzo[b]thienyl)ethyl]-L-valinamide
(Intermediate Compound No. 27)

11.3 g of $N^2$-tert-butoxycarbonyl-$N^1$-[1-(2-benzo[b]thienyl)ethyl]-L-valinamide was dissolved in 150 ml of ethyl acetate, and 20 ml of 6N hydrochloric acid was added to the resultant solution at room temperature. After agitating overnight at room temperature, the pH of the solution was adjusted to 7-8 with a saturated aqueous solution of sodium bicarbonate under water cooling. The ethyl acetate layer was then washed with water, dried over anhydrous magnesium sulfate, and concentrated to yield a crude product. This crude product was then refined on FLORISIL ® column chromatography to yield 6.7 g of the desired product, a white solid substance (melting point: 70°-71° C.).

Specific examples of intermediate [V] obtained through the operations of Reference Examples 5 and 6 are shown in Table 10.

TABLE 8

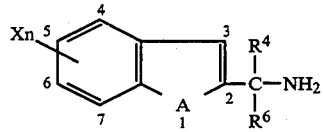

| Intermediate Compound No. | Xn | $R^4$ | $R^6$ | A | Melting Point (°C.) or Refractive Index ($n_D^{20}$) |
|---|---|---|---|---|---|
| 3 | 6-F | $CH_3$ | H | S | |
| 4 | 6-$CH_3$ | $CH_3$ | H | S | |
| 5 | 7-Cl | $CH_3$ | H | O | 1.5866 |
| 6 | 6-Cl | $CH_3$ | H | O | 1.5780 |
| 7 | 4-Cl | $CH_3$ | H | O | 1.5861 |
| 8 | 7-$CH_3$ | $CH_3$ | H | O | 1.5649 |
| 9 | 5-$CH_3$ | $CH_3$ | H | O | 1.5671 |
| 10 | 4-$CH_3$ | $CH_3$ | H | O | 1.5698 |
| 11 | 5-F | $CH_3$ | H | O | 1.5750 |
| 12 | 5-$CO_2CH_3$ | $CH_3$ | H | O | 1.5840 |
| 13 | 5-$OCF_3$ | $CH_3$ | H | O | not determined |
| 14 | 5-$SCH_3$ | $CH_3$ | H | O | 1.6109 |
| 15 | 5-CN | $CH_3$ | H | O | 49–52 |
| 16 | 5,6-$Cl_2$ | $CH_3$ | H | O | 1.5982 |
| 17 | 5-Cl, 4-$CH_3$ | $CH_3$ | H | O | 1.5780 |

TABLE 8-continued

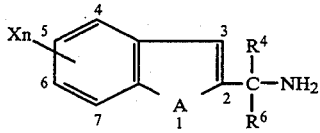

| Intermediate Compound No. | Xn | $R^4$ | $R^6$ | A | Melting Point (°C.) or Refractive Index ($n_D^{20}$) |
|---|---|---|---|---|---|
| 18 | H | $CH_3$ | $CH_3$ | O | |
| 19 | 5-Cl | $CH_3$ | $CH_3$ | O | 1.5693 |
| 20 | 5-F | $CH_3$ | H | S | 37–38 |

TABLE 9

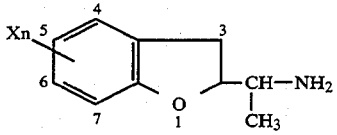

| Intermediate Compound No. | Xn | Refractive Index ($n_D^{20}$) |
|---|---|---|
| 22 | 5-Cl | 1.5580 |
| 23 | 5-F | 1.5316 |
| 24 | 5-$CH_3$ | 1.5402 |

TABLE 10

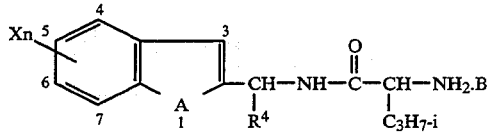

| Intermediate Compound No. | Xn | $R^4$ | A | B | Melting Point (°C.) |
|---|---|---|---|---|---|
| 28 | 5-Cl | $CH_3$ | O | HCl | 184–189 |
| 29 | 5-CN | $CH_3$ | O | HCl | 202–205 |
| 30 | 5-F | $CH_3$ | O | HCl | 90–93 |
| 31 | 3-$CH_3$ | $CH_3$ | S | | 58–62 |
| 32 | H | H | S | | 76–77 |

The methods for producing the compounds according to the present invention as well as the use of the compounds will be described in detail in the following examples.

EXAMPLE 1

Synthesis of
$N^2$-tert-butoxycarbonyl-$N^1$-[1-(5-cyano-2-benzofuranyl)ethyl]-L-valinamide (Compound No. 16)

0.4 g of N-methylpiperidine was added to a solution containing 0.8 g of N-tert-butoxycarbonyl-L-valine dissolved in 40 ml of dichloromethane, at −20° C. or lower. After the mixture was stirred for 10 minutes at the same temperature, 0.5 g of isobutyl chloroformate was added to the mixture at −40° C., and stirred for 1 hour between −40° C. and −15° C. 0.7 g of 1-(5-cyano-2-benzofuranyl)ethylamine was added to this mixture at −20° C., and then the reaction mixture was allowed to sit and warm naturally to room temperature, with stirring. Water was subsequently added to the reaction mixture. After the dichloromethane layer was washed successively with a 5% aqueous solution of sodium bicarbonate and water, the organic layer was dried over anhydrous magnesium sulfate and then condensed. The residue, which was a crude crystal, was purified by column chromatography on silica gel, thus obtaining 0.7 g of the desired product in the form of a white powder.

EXAMPLE 2

Synthesis of
$N^1$-[1-(5-chloro-2-benzofuranyl)ethyl]-$N^2$-isopropoxycarbonyl-L-valinamide (Compound Nos. 70, 71 and 296)

0.54 g of N-methylmorpholine, and subsequently 0.7 g of isopropyl chloroformate were added to a solution containing 1.57 g of N-[1-(5-chloro-2-benzofuranyl)ethyl]-2-amino-3-methylbutanamide hydrochloride dissolved in 40 ml of dichloromethane at −15° C. The mixture was allowed to sit and warm naturally to room temperature and stirred for 15 hours at room temperature. Water was subsequently added to the reaction mixture. After the dichloromethane layer was washed with water, the organic layer was dried over anhydrous magnesium sulfate and then concentrated. The residue, which was a crude crystal, was purified by column chromatography on silica gel, thus obtaining 0.85 g of the desired product in the form of a white powder.

0.8 g of the diastereomeric mixture obtained firm the above reaction was separated using liquid chromatography. The first eluted ingredient and the second eluted ingredient were condensed, thus obtaining 0.4 g of the desired diastereomer in the form of a white powder.

EXAMPLE 3

Synthesis of
$N^2$-isopropoxycarbonyl-$N^1$-[1-(5-nitro-2-benzofuranyl)ethyl]-L-valinamide (Compound No. 108)

0.17 g of N-methylmorpholine, and subsequently 0.18 g of isopropyl chloroformate were added to a solution containing 0.5 g of N-[1-(5-nitro-2-benzofuranyl)ethyl]-2-amino-3-methylbutanamide dissolved in 40 ml of dichloromethane, at −15° C. The mixture was allowed to sit and warm naturally to room temperature and stirred for 15 hours at room temperature. Water was subsequently added to the reaction mixture. After the dichloromethane layer was washed with water, the organic layer was dried over anhydrous magnesium sulfate and then concentrated. The residue, which was a crude crystal, was purified by column chromatography on silica gel, thus obtaining 0.1 g of the desired product in the form of a white powder.

EXAMPLE 4

Synthesis of
$N^1$-[1(5-fluoro-2-benzofuranyl)ethyl]-$N^2$-isopropoxycarbonyl-L-valinamide (Compound No. 115)

4.7 g of N-methylpiperidine was added to a solution containing 9.7 g of N-isopropoxycarbonyl-L-valine dissolved in 100 ml of dichloromethane, at −20° C. and the mixture was stirred for 15 minutes at the same temperature. Subsequently, 6.5 g of isobutyl chloroformate was added to the mixture at −30° C. and then the whole mixture was stirred between −30° C. and −20° C. for 30 minutes. 8.5 g of 1-(5-fluoro-2-benzofuranyl)ethylamine was then added to the mixture at −50° C. The mixture was allowed to sit and warm naturally to room temperature and then stirred for 15 hours at room temperature. Water was subsequently added to the reaction mixture. After the dichloromethane layer was washed with water, the organic layer was dried over anhydrous magnesium sulfate and then concentrated. The residue, which was a crude crystal, was purified by column chromatography on silica gel, thus obtaining 10.6 g of the desired product in the form of a white powder.

EXAMPLE 5

Synthesis of 2-tert-butoxycarbonylamino-N-[1-(5-chloro-2-benzofuranyl)ethyl]-2,3-dimethylbutanamide (Compound No. 140)

2.6 ml of a 1M aqueous solution of sodium bicarbonate and 0.62 g of di-tert-butyldicarbonate were added to a stirred solution containing 0.8 g of 2-amino-N-[1-(5-chloro-2-benzofuranyl)ethyl]-2,3-dimethylbutananamide dissolved in 15 ml of dioxane/water (2/1), at 0° C. The reaction mixture was stirred for 30 minutes at room temperature and then condensed. The residue was extracted with ethyl acetate and the organic layer was washed with water, subsequently dried over anhydrous magnesium sulfate and then concentrated under reduced pressure. The residue was purified by column chromatography on silica gel, thus obtaining 0.52 g of the desired product in the form of a white powder.

EXAMPLE 6

Synthesis of $N^1$-[1-(5-chloro-2-benzofuranyl)ethyl]-$N^2$-(N-methylanilinocarbonyl)-L-valinamide (Compound No. 151)

0.34 g of N-methylmorpholine and 0.57 g of N-methyl-N-phenylcarbamoyl chloride were successively added to a solution containing 1.1 g of N-[1-(5-chloro-2-benzofuranyl)ethyl]-2-amino-3-methylbutanamide hydrochloride dissolved in 30 ml of dichloromethane, at −15° C. The mixture was allowed to sit and warm naturally to room temperature and then stirred for 15 hours at room temperature. Water was subsequently added to the reaction mixture. After the dichloromethane layer was washed with water, the organic layer was dried over anhydrous magnesium sulfate and then concentrated. The residual crude crystal was purified by column chromatography on silica gel, thus obtaining 1.1 g of the desired product in the form of a white powder.

EXAMPLE 7

Synthesis of $N^2$-tert-butoxycarbonyl-$N^1$-{1-[3-methyl-2-benzo[b]-thienyl]ethyl}-L-valinamide (Compound No. 159)

0.5 g of N-methylpiperidine was added to a solution containing 1.3 g of N-tert-butoxycarbonyl-L-valine dissolved in 25 ml of dichloromethane, at −20° C. or lower. The reaction mixture was stirred at the same temperature for 10 minutes. Furthermore, 0.7 g of isobutyl chloroformate was added to the mixture at −40° C. and then stirred between −40° C. and −15° C. for 1 hour. 1.0 g of 1-[3-methyl-2-benzo[b]thienyl]ethylamine was added to the mixture at −20° C. The mixture was allowed to sit and warm naturally to room temperature with stirring. Water was subsequently added to the reaction mixture. After the dichloromethane layer was washed successively with a 5% aqueous solution of sodium bicarbonate and water, the organic layer was dried over anhydrous magnesium sulfate and then concentrated. The residual crude crystal was purified by column chromatography on silica gel, thus obtaining 0.8 g of the desired product as a white powder.

EXAMPLE 8

Synthesis of $N^1$-[1-(5-fluorobenzo[b]thiophen-2-yl)ethyl]-$N^2$-isopropoxycarbonyl-L-valinamide (Compound No. 192)

5.1 g of N-methylpiperidine was added to a solution containing 10.4 g of N-isopropoxycarbonyl-L-valine dissolved in 200 ml of dichloromethane, at −20° C. and then 7.0 g of isobutyl chloroformate was added dropwise to the mixture. After the mixture was stirred at −20° C. for 10 minutes, 10.0 g of 1-(5-fluorobenzo[b]thiophen-2-yl)ethylamine was added to the mixture at −50° C. After stirring at the same temperature, the mixture was allowed to sit and warm naturally to room temperature and then stirred for 15 hours at room temperature. After the reaction mixture was washed successively with 10% hydrochloric acid, a saturated aqueous solution of sodium bicarbonate, and water, the organic layer was then dried over anhydrous sodium sulfate and then concentrated under reduced pressure. The residue was purified by column chromatography on silica gel, thus obtaining 12.3 g of the desired product in the form of a white powder.

EXAMPLE 9

Synthesis of $N^2$-tert-butoxycarbonyl-$N^1$-[1-(3-methyl-2-indolyl)ethyl]-L-valinamide (Compound No. 240)

2.4 g of N-methylpiperidine was added to a solution containing 3.1 g of N-tert-butoxycarbonyl-L-valine dissolved in 80 ml of dichloromethane, at −20° C. or lower and then the mixture was stirred at the same temperature for 10 minutes. 2.0 g of isobutyl chloroformate was added to the mixture at −40° C. and the entire mixture was stirred between −40° C. and −15° C. for 1 hour. 2.5 g of 1-(3-methyl-2-indolyl)ethylamine was then added to the mixture at −20° C. The mixture was allowed to sit and warm naturally to room temperature and then stirred for 12 hours at room temperature. Water was subsequently added to the reaction mixture. After the dichloromethane layer was washed successively with a 5% aqueous solution of sodium bicarbonate and water, the organic layer was dried over anhydrous magnesium sulfate and then concentrated. The residue was purified by column chromatography on silica gel, thus obtaining 2.5 g of the desired product in the form of a white powder.

EXAMPLE 10

Synthesis of $N^2$-tert-butoxycarbonyl-$N^1$-[1-(2,3-dihydro-2-benzofuranyl)ethyl]-L-valanamide (Compound No. 387)

0.37 g of N-methylpiperidine was added to a solution containing 0.8 g of N-tert-butoxycarbonyl-L-valine dissolved in 20 ml of dichloromethane, at −20° C. or lower and then the mixture was stirred at the same temperature for 10 minutes. 0.51 g of isobutyl chloroformate was added to the mixture at −40° C. and the entire mixture was stirred between −40° C. and −15° C. for 1 hour. 0.6 g of 1-(2,3-dihydro-2-benzofuranyl)ethylamine was added to the mixture at −20° C. The mixture was allowed to sit and warm naturally to room temperature with stirring. Water was then added to the reaction mixture. After the dichloromethane layer was washed successively with a 5% aqueous solution of sodium bicarbonate and water, the organic layer was dried over anhydrous magnesium sulfate and then concentrated. The residual crude crystal was purified by column chromatography on silica gel, thus obtaining 0.5 g of the desired product in the form of a white powder.

EXAMPLE 11

Synthesis of N$^2$-tert-butoxycarbonyl-N$^1$-[1-(3-indolyl)ethyl]-L-valinamide (Compound No. 405)

0.7 g of N-methylpiperidine was added to a solution containing 1.5 g of N-tert-butoxycarbonyl-L-valine dissolved in 50 ml of dichloromethane, at −20° C. or lower and then the mixture was stirred at the same temperature for 10 minutes. 0.9 g of isobutyl chloroformate was added to the mixture at −40° C. and the entire mixture was stirred at −40° C.−−15° C. for 1 hour. 1.1 g of 1-(3-indolyl)ethylamine was added to the mixture at −20° C. The mixture was allowed to sit and warm naturally to room temperature and then stirred at room temperature for 12 hours. Water was subsequently added to the reaction mixture. After the dichloromethane layer was washed successively with a 5% aqueous solution of sodium bicarbonate and water, the organic layer was dried over anhydrous magnesium sulfate and then concentrated. The residual crude crystal was purified by column chromatography on silica gel, thus obtaining 0.4 g of the desired product in the form of a reddish-brown powder.

The agricultural or horticultural fungicide according to the present invention is a composition containing a condensed heterocyclic derivative represented by formula [I] as an active ingredient. In the case where the compounds according to the present invention are employed as an agricultural or horticultural fungicide, the compounds acting as the active ingredient can be formulated appropriately, depending on the purpose. The active ingredient is usually diluted in an inert liquid or a solid carrier, and a surfactant, a dispersant, an adjuvant, and the like are added thereto if necessary. The mixture is then formulated in a known manner into, for example, a fine powder, a wettable powder, an emulsifiable concentrate, granules, or the like.

Suitable examples of carriers employed in the formulation are solid carriers such as talc, bentonite, clay, kaolin, diatomaceous earth, white carbon, vermiculite, slaked lime, siliceous sand, ammonium sulfate, urea, or the like; and liquid carriers such as isopropyl alcohol, xylene, cyclohexanone, methylnaphthalene, and the like. Illustrative examples of the surfactants and dispersants include salts of dinaphthylmethanesulfonic acid, alkylarylsulfonic acid, and ligninesulfonic acid, sulfate esters of alcohol, polyoxyethylene glycol ethers, polyoxyethylene alkyl aryl ethers, polyoxyethylenesorbitan monoalkylates, and the like. Suitable examples of auxiliary agents include carboxymethylcellulose, and the like. These preparations can be applied directly, or after diluting the preparation to a suitable concentration.

The agricultural or horticultural fungicide according to the present invention can be employed for a number of purposes: for example, treating seeds, spraying of stem and leaf portions, injection into the applying water, and applying into the soil. The proportion of the active ingredient is selected as needed. When formulated into a fine powder or granules, 0.1% by weight to 20% by weight of the active ingredient is preferred. For an emulsifiable concentrate or wettable powder, 5% by weight to 80% by weight of the active ingredient is adequate.

The rate of application of the agricultural or horticultural fungicide according to the present invention may vary depending on the type of active compound employed, the kind of the pest or disease to be controlled, the nature of occurrence of the pest or disease, the degree of damage, environmental conditions, the form of preparation to be used, and the like. When the agricultural or horticultural fungicide of the present invention is applied directly in the form of fine powder or granules, it is recommended that the rate of application of the active ingredient be suitably chosen within the range of 0.1 g to 5 kg per 10 ares, preferably, in the range of 1 g to 1 kg per 10 ares. In addition, when the fungicide of the present invention is in the form of a liquid such as an emulsifiable concentrate or a wettable powder, it is recommended that the ratio for application of the active ingredient be suitably chosen within the range of 0.1 ppm to 10,000 ppm, and preferably within the range of 10 ppm to 3,000 ppm.

The compounds according to the present invention in the formulation described above can control plant diseases caused by fungi belonging to Oomycetes, Ascomycetes, Deuteromycetes, and Basidiomycetes or other pathogenic fungi. The fungi include, but are not limited to, Pseudoperonospora such as cucumber downy mildew (*Pseudoperonospora cubensis*), Phytophthora such as tomato late blight (*Phytophthora infestans*), and Plasmopara such as grape downy mildew (*Plasmopara viticola*).

The agricultural or horticultural fungicide according to the present invention may be employed alone or in combination with other fungicides, insecticides, herbicides, plant growth modifiers, fertilizers or the like.

Next, the representative formulations are illustrated with reference to the following Formulation Examples, wherein all "%" represent "percent by weight".

FORMULATION EXAMPLE 1

Fine powder

Two % of Compound (59), 5% of diatomaceous earth, and 93% of clay were uniformly mixed and ground into a fine powder.

FORMULATION EXAMPLE 2

Wettable powder

Fifty % of Compound (70), 45% of diatomaceous earth, 2% of sodium dinaphthylmethanedisulfonate, and 3% of sodium ligninsulfonate were uniformly mixed and ground into a wettable powder.

FORMULATION EXAMPLE 3

Emulsifiable concentrate

Thirty % of Compound (5), 20% of cyclohexanone, 11% of polyoxyethylene alkylaryl ether, 4% of calcium alkylbenzenesulfonate, and 35% of methylnaphthalene were uniformly dissolved, thus obtaining an emulsifiable concentrate.

FORMULATION EXAMPLE 4

Granules

Five % of Compound (16), 2% of sodium lauryl sulfonate, 5% of sodium lignin sulfonate, 2% of carbomethylcellulose, and 86% of clay were mixed and ground. One hundred parts by weight of the ground n-fixture was added to 20 parts by weight of water. The resulting mixture was kneaded and formed into granules of 14 mesh to 32 mesh by means of an extrusion granulator, and then dried into the desired granules.

EFFECT OF THE INVENTION

The agricultural or horticultural fungicides according to the present invention exhibit high ability to control the growth or spread of cucumber downy mildew (*Pseudoperonospora cubensis*), tomato late blight (*Phytophthora infestans*), and grape downy mildew (*Plasmopara viticola*), and are effective for potato late blight (*Phytophthora infestans*). In addition, the agricultural or horticultural fungicides according to the present invention not only exhibit the ability to present fungal infection, but also exhibit the ability to eliminate pathogenic fungi after it has invaded a host plant. Furthermore, the agricultural or horticultural fungicides of the present invention are also characterized in that they are not harmful chemicals and exhibit excellent characteristics such as systemic action, residual activity, and the influence of rain-fall on effect.

The effects of the compounds according to the present invention are now illustrated with reference to the following Test Examples.

TEST EXAMPLE 1

Test on the Effect of Preventing Infection by Cucumber Downy Mildew (*Pseudoperonospora cubensis*)

Cucumber seeds (variety: "*Sagami hanjiro*") were sown at a rate of 10 seeds each in a square PVC(polyvinyl chloride) pot, wherein each side is 9 cm wide. The seeds were allowed to grow in a greenhouse, for 7 days, to the cotyledonous stage. A wettable powder prepared as in Formulation Example 2 was diluted with water to a concentration of 500 ppm of the active ingredient, and the aqueous preparation obtained was then applied at a rate of 10 ml per pot to the cucumber seedlings at their cotyledonous stage. After drying in the air, the plant was inoculated with a spore suspension of cucumber downy mildew (*Pseudoperonospora cubensis*) fungi and then placed in a moist chamber at 22° C. for 24 hours, and then placed in a green house. On the seventh day after the inoculation, the extent of lesion was rated in accordance with the following standards of evaluation in order to secure the preventive effects of the compounds according to the present invention. The results of the test are given in Table 11.

Standards of Evaluation:
Class A: No lesions were observed.
Class B: Incidence area is less than 25%.
Class C: Incidence area is 25% or more and less than 50%.
Class D: Incidence area is 50% or more.

For comparison, $N^2$-(t-butoxycarbonyl)-$N^1$-(3-pyridylmethyl)-L-valinamide (Comparative Compound A, hereinafter referred to as "CA") and $N^2$-(phenoxycarbonyl)-$N^1$-[1-(2-furyl)ethyl]-L-valinamide (Comparative Compound B, hereinafter referred to as "CB") which are disclosed as active ingredients for fungicides in Japanese Patent Application First Publication No. Hei 3-5451 and Japanese Patent Application First Publication No. Hei 3-153657, respectively, were employed. These comparative compounds were formulated in a similar manner as the compounds of the present invention to be tested.

TABLE 11

| Compound No. | Evaluation |
| --- | --- |
| 1 | A |
| 2 | A |
| 4 | B |
| 5 | A |
| 6 | A |
| 7 | B |
| 8 | B |
| 9 | B |
| 10 | A |
| 11 | A |
| 12 | A |
| 13 | A |
| 14 | B |
| 15 | A |
| 16 | A |
| 17 | A |
| 18 | A |
| 19 | A |
| 20 | A |
| 23 | A |
| 25 | A |
| 27 | B |
| 28 | B |
| 29 | B |
| 33 | A |
| 40 | B |
| 55 | A |
| 56 | A |
| 58 | A |
| 59 | A |
| 60 | A |
| 61 | A |
| 63 | A |
| 64 | B |
| 66 | B |
| 67 | A |
| 68 | A |
| 69 | A |
| 70 | A |
| 71 | A |
| 72 | A |
| 73 | B |
| 76 | A |
| 77 | A |
| 79 | A |
| 80 | A |
| 83 | A |
| 90 | B |
| 92 | A |
| 93 | A |
| 94 | B |
| 97 | A |
| 99 | A |
| 100 | A |
| 101 | A |
| 102 | A |
| 104 | A |
| 105 | A |
| 106 | A |
| 107 | A |
| 108 | A |
| 109 | A |
| 110 | A |
| 111 | A |
| 112 | A |
| 114 | A |
| 115 | A |
| 116 | A |
| 117 | A |
| 118 | A |
| 119 | A |
| 120 | A |
| 121 | A |
| 128 | B |
| 151 | B |
| 156 | A |
| 157 | A |
| 158 | A |
| 159 | A |
| 161 | A |
| 163 | A |

TABLE 11-continued

| Compound No. | Evaluation |
| --- | --- |
| 165 | A |
| 166 | A |
| 167 | A |
| 168 | A |
| 169 | A |
| 170 | A |
| 171 | B |
| 177 | A |
| 178 | A |
| 179 | A |
| 180 | A |
| 181 | A |
| 182 | B |
| 192 | A |
| 193 | A |
| 194 | A |
| 200 | A |
| 204 | A |
| 205 | A |
| 206 | B |
| 228 | A |
| 230 | B |
| 233 | A |
| 234 | A |
| 235 | B |
| 304 | B |
| 307 | B |
| 313 | A |
| 314 | A |
| 315 | B |
| 316 | A |
| 217 | A |
| 318 | A |
| 319 | A |
| 320 | A |
| 321 | A |
| 322 | B |
| 323 | B |
| 324 | A |
| 325 | A |
| 326 | A |
| 327 | A |
| 328 | B |
| 330 | A |
| 331 | A |
| 332 | B |
| 335 | A |
| 336 | A |
| 337 | A |
| 344 | A |
| 350 | B |
| 351 | A |
| 352 | A |
| 353 | A |
| 356 | A |
| 357 | A |
| 358 | A |
| 359 | A |
| 360 | A |
| 362 | A |
| 363 | A |
| 364 | A |
| 365 | A |
| 366 | A |
| 367 | A |
| 368 | A |
| 370 | A |
| 376 | A |
| 377 | A |
| 378 | A |
| 380 | A |
| 381 | A |
| 382 | A |
| 383 | A |
| 384 | A |
| 385 | A |
| 386 | A |
| 387 | A |
| 388 | A |
| 389 | A |
| 393 | A |
| 395 | A |
| 397 | A |
| 398 | A |
| 399 | A |
| 401 | A |
| 402 | A |
| 403 | A |
| 404 | A |
| 407 | A |
| 413 | A |
| 414 | A |
| 423 | B |
| CA | D |
| CB | D |

TEST EXAMPLE 2

Test on the Effect of Treating Infection by Cucumber Downy Mildew (*Pseudoperonospora cubensis*)

Cucumber seeds (variety: "*Sagami hanjiro*") were sown at a rate of 10 seeds each in a square PVC (polyvinyl chloride) pot, wherein each side is 9 cm wide. The seeds were allowed to grow in a greenhouse, for 7 days, to the cotyledonous stage. The seedlings were inoculated with a spore suspension of cucumber downy mildew (*Pseudoperonospora cubensis*) fungi and then placed in a moist chamber at 22° C. for 24 hours. After drying in the air, a wettable powder prepared as in Formulation Example 2 was diluted with water to a concentration of 500 ppm of the active ingredient, and the aqueous preparation obtained was then applied at a rate of 10 ml per pot to the cucumber seedlings. The seedlings were then placed in a green house. On the seventh day after the inoculation, the extent of lesion was rated in accordance with the following standards of evaluation in order to secure the effect of treating with the compounds according to the present invention. The same Comparative Compounds as disclosed in Test Example 1 were employed. The results of the test are given in Table 12.

Evaluation standards:
Class A: No lesions were observed.
Class B: Incidence area is less than 25%.
Class C: Incidence area is 25% or more and less than 50%.
Class D: Incidence area is 50% or more.

TABLE 12

| Compound No. | Evaluation |
| --- | --- |
| 6 | B |
| 12 | B |
| 13 | B |
| 16 | A |
| 17 | A |
| 19 | B |
| 23 | A |
| 25 | B |
| 33 | A |
| 58 | A |
| 59 | A |
| 60 | A |
| 63 | B |
| 68 | A |
| 69 | B |
| 70 | A |
| 71 | A |
| 72 | A |
| 76 | A |
| 77 | B |
| 80 | A |
| 83 | B |

TABLE 12-continued

| Compound No. | Evaluation |
| --- | --- |
| 97 | A |
| 99 | B |
| 100 | B |
| 101 | A |
| 102 | A |
| 104 | A |
| 105 | A |
| 107 | A |
| 108 | A |
| 109 | A |
| 112 | A |
| 114 | B |
| 115 | A |
| 116 | A |
| 117 | A |
| 119 | A |
| 120 | A |
| 157 | A |
| 158 | B |
| 161 | B |
| 163 | A |
| 165 | A |
| 169 | A |
| 177 | B |
| 179 | B |
| 180 | A |
| 192 | A |
| 193 | B |
| 194 | A |
| 200 | A |
| 204 | A |
| 233 | B |
| 313 | A |
| 316 | A |
| 317 | A |
| 319 | A |
| 320 | A |
| 321 | A |
| 325 | B |
| 326 | A |
| 327 | A |
| 331 | B |
| 335 | A |
| 336 | B |
| 337 | A |
| 344 | A |
| 351 | A |
| 352 | A |
| 353 | A |
| 356 | B |
| 357 | A |
| 358 | A |
| 359 | A |
| 360 | A |
| 362 | A |
| 363 | A |
| 370 | A |
| 376 | A |
| 380 | A |
| 381 | B |
| 382 | A |
| 383 | B |
| 387 | A |
| 388 | A |
| 389 | A |
| 393 | A |
| 395 | A |
| 397 | A |
| 398 | A |
| 399 | A |
| 401 | A |
| 402 | A |
| 403 | A |
| 414 | B |
| CA | D |
| CB | D |

TEST EXAMPLE 3

Test on the Effect of Preventing Infection by Tomato Late Blight (*Phytophthora infestans*)

One tomato seedling (variety: "Ponterosa") was transplanted in each porcelain pot (diameter: 9 cm) and grown in a greenhouse. A wettable powder prepared as in Formulation Example 2 was diluted with water to a concentration of 500 ppm of the active ingredient, and the aqueous preparation obtained was then applied at a rate of 20 ml per pot to the tomato seedlings at their 6- or 7-leaf stage. After drying in the air, the plant was inoculated with a zoosporangium suspension of tomato late blight (*Phytophthora infestans*) fungi and then placed in a moist chamber at 22° C. On the fourth day after the inoculation, index of incidence was determined based on the incidence area. The degree of damage and the ability to prevent the disease (controlling activity) were calculated according to the following standards. The results of the test are shown in Table 13. The same Comparative Compounds (CA and CB) as disclosed in Test Example 1 were employed.

Standard of Test

Incidence Index 0: No lesions
Incidence Index 1: Incidence area is less than 5%
Incidence Index 2: Incidence area is 5% or more and less than 33.3%
Incidence Index 3: Incidence area is 33.3% or more and less than 66.6%
Incidence Index 4: Incidence area is 66.6% or more $$\text{Degree of Damage (\%)} = \frac{\Sigma(\text{Incidence Index} \times \text{Number of Proper Leaves})}{4 \times \text{Number of Leaves Examined}} \times 100$$

$$\text{Controlling Activity (\%)} = \left(1 - \frac{\text{Degree of Damage}}{\text{Degree of Damage in Untreated Plot}}\right) \times 100$$

TABLE 13

| Compound No. | Controlling Activity (%) |
| --- | --- |
| 2 | 100 |
| 6 | 100 |
| 16 | 100 |
| 17 | 100 |
| 20 | 100 |
| 23 | 100 |
| 25 | 100 |
| 33 | 100 |
| 55 | 100 |
| 56 | 100 |
| 58 | 100 |
| 59 | 100 |
| 60 | 100 |
| 63 | 100 |
| 67 | 100 |
| 68 | 100 |
| 69 | 100 |
| 70 | 100 |
| 71 | 100 |
| 72 | 100 |
| 76 | 100 |
| 77 | 100 |
| 79 | 100 |
| 80 | 100 |
| 83 | 100 |
| 92 | 100 |
| 93 | 100 |
| 97 | 100 |
| 99 | 100 |

TABLE 13-continued

| Compound No. | Controlling Activity (%) |
|---|---|
| 100 | 100 |
| 101 | 100 |
| 102 | 100 |
| 104 | 100 |
| 105 | 100 |
| 106 | 100 |
| 107 | 100 |
| 108 | 100 |
| 109 | 100 |
| 110 | 100 |
| 111 | 100 |
| 112 | 100 |
| 114 | 100 |
| 115 | 100 |
| 116 | 100 |
| 117 | 100 |
| 118 | 100 |
| 119 | 100 |
| 120 | 100 |
| 121 | 100 |
| 156 | 100 |
| 157 | 100 |
| 158 | 100 |
| 159 | 100 |
| 161 | 100 |
| 163 | 100 |
| 165 | 100 |
| 166 | 100 |
| 169 | 100 |
| 177 | 100 |
| 178 | 100 |
| 179 | 100 |
| 180 | 100 |
| 192 | 100 |
| 193 | 100 |
| 194 | 100 |
| 200 | 100 |
| 204 | 100 |
| 233 | 100 |
| 234 | 100 |
| 313 | 100 |
| 314 | 100 |
| 316 | 100 |
| 317 | 100 |
| 319 | 100 |
| 320 | 100 |
| 321 | 100 |
| 325 | 100 |
| 327 | 100 |
| 331 | 100 |
| 335 | 100 |
| 336 | 100 |
| 337 | 100 |
| 344 | 100 |
| 351 | 100 |
| 352 | 100 |
| 353 | 100 |
| 356 | 100 |
| 357 | 100 |
| 358 | 100 |
| 359 | 100 |
| 360 | 100 |
| 362 | 100 |
| 363 | 100 |
| 364 | 100 |
| 366 | 100 |
| 367 | 100 |
| 368 | 100 |
| 370 | 100 |
| 376 | 100 |
| 377 | 100 |
| 378 | 100 |
| 380 | 100 |
| 381 | 100 |
| 382 | 100 |
| 383 | 100 |
| 384 | 100 |
| 385 | 100 |
| 386 | 100 |
| 387 | 100 |
| 388 | 100 |
| 389 | 100 |
| 393 | 100 |
| 395 | 100 |
| 397 | 100 |
| 398 | 100 |
| 399 | 100 |
| 401 | 100 |
| 402 | 100 |
| 403 | 100 |
| CA | 2 |
| CB | 5 |

TEST EXAMPLE 4

Test on the Effect of Preventing Infection by Grape Downy Mildew (*Plasmopara viticola*)

One grape seedling (variety: "Kyoho") each was grown by cutting and pruned in a porcelain pot (diameter: 12 cm) and maintained in a greenhouse. A wettable powder prepared as in Formulation Example 2 was diluted with water to a concentration of 500 ppm of the active ingredient, and the aqueous preparation obtained was then applied at a rate of 20 ml per pot to the grape seedlings at their 4- or 5-leaf stage. After drying in the air, the plant was inoculated with a zoosporangium suspension of grape downy mildew (*Plasmopara viticola*) fungi and then placed in a moist chamber at 22° C. for 24 hours. On the seventh day in the greenhouse after the inoculation, the plant was again placed in a moist chamber at 22° C. for 24 hours to cultivate conidiospores. The incidence area where conidiospores were grown in each leaf was examined and determined the incidence index according to the following standards. The degree of damage and ability to prevent the disease (controlling activity) were calculated in the same manner as described in Test Example 3. The results of the test are shown in Table 14. The same Comparative Compounds as disclosed in Test Example 1 were employed.

Standard of Test

Incidence Index 0: No lesions

Incidence Index 1: Incidence area is less than 5%

Incidence Index 2: Incidence area is 5% or more and less than 33.3%

Incidence Index 3: Incidence area is 33.3% or more and less than 66.6%

Incidence Index 4: Incidence area is 66.6% or more

TABLE 14

| Compound No. | Controlling Activity (%) |
|---|---|
| 2 | 100 |
| 6 | 100 |
| 16 | 100 |
| 17 | 100 |
| 20 | 100 |
| 23 | 100 |
| 25 | 100 |
| 33 | 100 |
| 55 | 100 |
| 56 | 100 |
| 58 | 100 |
| 59 | 100 |
| 60 | 100 |
| 63 | 100 |
| 67 | 100 |
| 68 | 100 |
| 69 | 100 |
| 70 | 100 |
| 71 | 100 |
| 72 | 100 |
| 76 | 100 |

TABLE 14-continued

| Compound No. | Controlling Activity (%) |
|---|---|
| 77 | 100 |
| 79 | 100 |
| 80 | 100 |
| 83 | 100 |
| 92 | 100 |
| 93 | 100 |
| 97 | 100 |
| 99 | 100 |
| 100 | 100 |
| 101 | 100 |
| 102 | 100 |
| 104 | 100 |
| 105 | 100 |
| 106 | 100 |
| 107 | 100 |
| 108 | 100 |
| 109 | 100 |
| 110 | 100 |
| 111 | 100 |
| 112 | 100 |
| 114 | 100 |
| 115 | 100 |
| 116 | 100 |
| 117 | 100 |
| 118 | 100 |
| 119 | 100 |
| 120 | 100 |
| 121 | 100 |
| 156 | 100 |
| 157 | 100 |
| 158 | 100 |
| 159 | 100 |
| 161 | 100 |
| 163 | 100 |
| 165 | 100 |
| 166 | 100 |
| 169 | 100 |
| 177 | 100 |
| 178 | 100 |
| 179 | 100 |
| 180 | 100 |
| 192 | 100 |
| 193 | 100 |
| 194 | 100 |
| 200 | 100 |
| 204 | 100 |
| 233 | 100 |
| 234 | 100 |
| 313 | 100 |
| 314 | 100 |
| 316 | 100 |
| 317 | 100 |
| 319 | 100 |
| 320 | 100 |
| 321 | 100 |
| 325 | 100 |
| 327 | 100 |
| 331 | 100 |
| 335 | 100 |
| 336 | 100 |
| 337 | 100 |
| 344 | 100 |
| 351 | 100 |
| 352 | 100 |
| 353 | 100 |
| 356 | 100 |
| 357 | 100 |
| 358 | 100 |
| 359 | 100 |
| 360 | 100 |
| 362 | 100 |
| 363 | 100 |
| 364 | 100 |
| 366 | 100 |
| 367 | 100 |
| 368 | 100 |
| 370 | 100 |
| 376 | 100 |
| 377 | 100 |
| 378 | 100 |
| 380 | 100 |

TABLE 14-continued

| Compound No. | Controlling Activity (%) |
|---|---|
| 381 | 100 |
| 382 | 100 |
| 383 | 100 |
| 384 | 100 |
| 385 | 100 |
| 386 | 100 |
| 387 | 100 |
| 388 | 100 |
| 389 | 100 |
| 393 | 100 |
| 395 | 100 |
| 397 | 100 |
| 398 | 100 |
| 399 | 100 |
| 401 | 100 |
| 402 | 100 |
| 403 | 100 |
| CA | 7 |
| CB | 52 |

What is claimed is:

1. A condensed heterocyclic derivative represented by a formula:

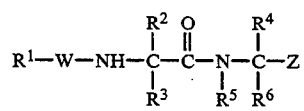

wherein $R^1$ represents a C1–C6 alkyl group optionally having at least one substituent selected from the group consisting of a halogen atom, a cyano group, and a methoxy group, a C2–C6 alkenyl group, a C2–C6 alkynyl group, a C3–C8 cycloalkyl group optionally having at least one methyl group, a C3–C8 cycloalkenyl group optionally having at least one methyl group, a C2–C6 cyclic ether group optionally having at least one methyl group, a C7–C10 aralkyl group optionally having at least one substituent selected from the group consisting of a methyl group, a methoxy group, and a nitro group, a phenyl group optionally having at least one substituent selected from the group consisting of a halogen atom, a methyl group, a methoxy group, a nitro group, and a methoxycarbonyl group, a dimethylamino group, or an ethoxy carbonyl group, $R^2$, $R^3$, $R^4$, $R^5$, and $R^6$ independently represent a hydrogen atom, a C1–C6 alkyl group optionally having at least one halogen group, a C3–C6 cycloalkyl group, a C7–C10 aralkyl group; a phenyl group, a cyano group, an acyl group, a C1–C6 alkoxy group, or a C1–C6 alkoxycarbonyl group, $R^2$ may form a C3–C6 alkylic ring with $R^3$;

Z is represented by the following formulae:

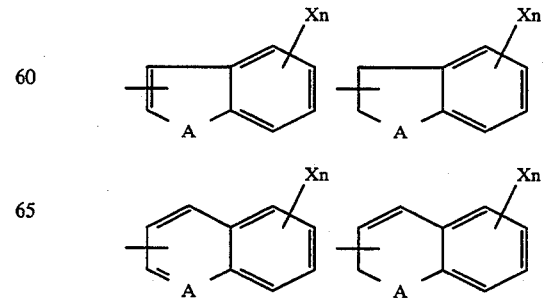

-continued

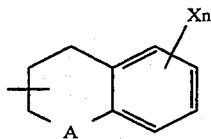

wherein
X represents a hydrogen atom, a halogen atom, a C1-C6 alkyl group optionally having at least one halogen atom, a C2-C6 alkynyl group, a methoxy group, a trifluoromethoxy group, a hydroxyl group, a methoxycarbonyl group, a methylcarbonyloxy group, an amino group, a dimethylamino group, a nitro group, a methylthio group, a methylsulfinyl group, a methylsulfonyl group, a phenyl group, an acetyl group, a formyl group, or a cyano group;
n is an integer of 1, 2, or 3;
A is O, S, N, or represented by the formula:

wherein
$R^7$ represents a hydrogen atom, a methyl group, an acetyl group, or a benzoyl group; and
W is represented by —C(O)—, —SO$_2$—, —NHC(O)—, —N(CH$_3$)C(O)—, —OC(O)—, —SC(O)—, —OC(S)—, or —SC(S)—.

2. A condensed heterocyclic derivative as recited in claim 1, wherein
$R^1$ represents a C2-C6 straight or branched alkyl group, a C3 straight or branched alkenyl group, a C5-C6 cycloalkyl group, or a phenyl group,
$R^2$ represents a hydrogen atom,
$R^3$ represents an ethyl group, an isopropyl group, or a sec-butyl group,
$R^4$ represents a hydrogen atom, a methyl group, an ethyl group, or a phenyl group,
$R^5$ represents a hydrogen atom, or a methyl group,
$R^6$ represents a hydrogen atom,
Z represents a substituted heterocyclic group including a benzofuran group, a benzothiophene group, an indole group, or a 2,3-dihydrobenzofuran which has one or two substituent selected from the group consisting of a fluorine atom, a chlorine atom, a nitro group, a cyano group, and a methyl group,
W is represented by —OC(O)—, and
wherein the carbon to which $R^2$ and $R^3$ are attached is in the S configuration.

3. A condensed heterocyclic derivative as recited in claim 1, wherein
$R^1$ represents an isopropyl group, a tert-butyl group, a sec-butyl group, a cyclopentyl group, an isopropenyl group, or a phenyl group,
$R^2$ represents a hydrogen atom,
$R^3$ represents an ethyl group, an isopropyl group, or a sec-butyl group,
$R^4$ represents a methyl group,
$R^5$ represents a hydrogen atom,
$R^6$ represents a hydrogen atom,
Z represents a substituted heterocyclic group including a benzofuran group or a benzothiophene which has one or two substituent selected from the group consisting of a fluorine atom, a chlorine atom, a nitro group, a cyano group, and a methyl group,
W is represented by —OC(O)—, and
wherein the carbon to which $R^2$ and $R^3$ are attached is in the S configuration.

4. A condensed heterocyclic derivative as recited in claim 1, wherein the derivative includes $N^1$-[1-(5-chloro-2-benzofuranyl)ethyl]-$N^2$-cyclopentyloxycarbonyl-L-valinamide, $N^1$-[1-(5-chloro-2-benzofuranyl)ethyl]-$N^2$-isopropyloxycarbonyl-L-valinamide, $N^1$-[1-(5-fluoro-2-benzofuranyl)ethyl]-$N^2$-isopropyloxycarbonyl-L-valinamide, $N^2$-isopropyloxycarbonyl-$N^1$-[1-(5-nitro-2-benzofuranyl)ethyl]-L-valinamide, $N^1$-[1-(5-fluoro-2-benzo[b]thienyl)ethyl]-$N^2$-isopropyloxycarbonyl-L-valinamide, $N^1$-[1-(6-fluoro-2-benzo[b]thienyl)ethyl]-$N^2$-isopropyloxycarbonyl-L-valanimide, $N^2$-sec-butyloxycarbonyl-$N^1$-[1-(5-chloro-2-benzofuranyl)ethyl]-L-valinamide, or $N^1$-[1-(5-chloro-2-benzofuranyl)ethyl]-$N^2$-phenoxycarbonyl-L-valinamide.

5. An agricultural or horticultural fungicide which comprises an effective amount of a condensed heterocyclic derivative, as recited in claim 1, known to be effective as a fungicide and a diluent.

6. A method for controlling fungi which infect agricultural or horticultural nonfungal, photosynthetic plants comprising the step of applying an effective amount of a condensed heterocyclic derivative, as recited in claim 1, known to be effective as a fungicide to the plants.

* * * * *